(12) United States Patent
Klein et al.

(10) Patent No.: US 7,884,126 B2
(45) Date of Patent: Feb. 8, 2011

(54) INDAZOLE-HETEROARYL DERIVATIVES

(75) Inventors: Markus Klein, Darmstadt (DE); Rolf Gericke, Seeheim-Jugenheim (DE); Werner Mederski, Zwingenberg (DE); Norbert Beier, Reinheim (DE); Florian Lang, Tuebingen (DE)

(73) Assignee: Merck Patent GmbH, Darmstadt (DE)

( * ) Notice: Subject to any disclaimer, the term of this patent is extended or adjusted under 35 U.S.C. 154(b) by 155 days.

(21) Appl. No.: 12/278,307

(22) PCT Filed: Jan. 10, 2007

(86) PCT No.: PCT/EP2007/000171

§ 371 (c)(1), (2), (4) Date: Aug. 5, 2008

(87) PCT Pub. No.: WO2007/090493

PCT Pub. Date: Aug. 16, 2007

(65) Prior Publication Data

US 2009/0076091 A1    Mar. 19, 2009

(30) Foreign Application Priority Data

Feb. 6, 2006  (DE) .................. 10 2006 005 180

(51) Int. Cl.
*A61K 31/341*   (2006.01)
*A61K 31/4045*  (2006.01)
*C07D 307/48*   (2006.01)
*C07D 231/56*   (2006.01)

(52) U.S. Cl. .................... 514/414; 514/461; 548/362.1; 549/473

(58) Field of Classification Search ................ 514/414, 514/461; 548/362.1; 549/473
See application file for complete search history.

(56) References Cited

U.S. PATENT DOCUMENTS

2007/0232620 A1 * 10/2007 Dorsch et al. .......... 514/255.05

FOREIGN PATENT DOCUMENTS

| WO | WO 03/051847 A1 | 6/2003 |
| WO | WO 2004/062662 A1 | 7/2004 |
| WO | WO 2005/123688 A2 | 12/2005 |
| WO | WO 2005123688 A2 * | 12/2005 |

OTHER PUBLICATIONS

Wu and Farrelly, Toxicology 236:1-6, 2007.*

* cited by examiner

*Primary Examiner*—Yong Chu
(74) *Attorney, Agent, or Firm*—Millen, White, Zelano & Branigan, P.C.

(57) ABSTRACT

The invention relates to novel indazole derivatives as cited in claim 1, which are inhibitors of CHK1, CHK2 and SGK kinases and can be used to treat cancer and other diseases.

3 Claims, No Drawings

INDAZOLE-HETEROARYL DERIVATIVES

BACKGROUND OF THE INVENTION

The present invention relates to compounds and to the use of compounds in which the inhibition, regulation and/or modulation of signal transduction by kinases, in particular tyrosine kinases and/or serine/threonine kinases, plays a role, furthermore to pharmaceutical compositions which comprise these compounds, and to the use of the compounds for the treatment of kinase-induced diseases.

The present invention relates to compounds in which the inhibition, regulation and/or modulation, in particular, of CHK1 and CHK2 kinase and of the cell volume-regulated human kinase h-sgk (human serum and glucocorticoid dependent kinase or SGK) plays a role, furthermore to pharmaceutical compositions which comprise these compounds, and to the use of the compounds for the treatment of CHK1-, CHK2- and SGK-induced diseases.

Cell cycle checkpoints are regulatory pathways that control the sequence and timing of cell cycle transitions. They ensure that important events, such as DNA replication and chromosome segregation, are completed with high reliability. The control of these cell cycle checkpoints is an important determinant of the manner in which tumour cells respond to many chemotherapies and radiation. Many effective cancer therapies work by causing DNA damage; however, resistance to these agents remains a considerable limitation in the treatment of cancer. There are various mechanisms of drug resistance; an important one is attributed to the prevention of cell cycle progression through the control of critical activation of a checkpoint pathway that arrests the cell cycle to provide time for repair and induces the transcription of genes to facilitate repair, thereby avoiding immediate cell death.

There are two of these checkpoints in the cell cycle—the G1/S checkpoint which is controlled by p53, and the G2/M checkpoint, which is monitored by the Ser/Thr kinase checkpoint kinase 1 (CHK1).

By abrogating checkpoint arrests at, for example, the G2 checkpoint, it may be possible to synergistically improve tumour cell death induced by DNA damage and circumvent resistance, (Shyjan et al, U.S. Pat. No. 6,723,498 (2004)). Human CHK1 plays a role in controlling cell cycle arrest by phosphorylating the phosphatase cdc25 on serine 216, which may possibly be involved in preventing activation of cdc2/cyclin B and initiating mitosis. (Sanchez et al. Science, 277: 1497 (1997)) Inhibition of CHK1 should therefore enhance the action of DNA-damaging substances by initiating mitosis before DNA repair is complete and thereby causing tumour cell death.

An approach to the design of chemosensitisers which abrogate the G2/M checkpoint consists in developing inhibitors of the key G2/M regulatory kinase CHK1. The fact that this approach works has been demonstrated in a number of proof-of-concept studies (Koniaras et al., *Oncogene*, 2001, 20:7453; Luo et al., *Neoplasia*, 2001, 3:411; Busby et al., *Cancer Res.*, 2000, 60:2108; Jackson et al., *Cancer Res.*, 2000, 60:566).

A further essential checkpoint kinase that may be mentioned, which plays a crucial role in p53-dependent apoptosis, is CHK2. The inhibition of CHK2 can protect normal sensitive tissue against chemotherapeutic agents (B.-B S. Zhou et al., *Progress in Cell Cycle Research*, Vol. 5, 413-421, 2003).

It can be shown for the compounds according to the invention that they inhibit the checkpoint kinase activity. It can be shown for checkpoint kinase inhibitors that they enable the cells to advance inappropriately to the metaphase of mitosis, which results in apoptosis of the cells concerned, and therefore have antiproliferative actions. The compounds according to the invention can be used for the treatment of neoplastic disease. The compounds according to the invention and salts thereof can be used against neoplastic diseases, such as carcinoma of the brain, breast, ovaries, lung, intestine, prostate, skin or other tissue, and against leukaemia and lymphomas, tumours of the central and peripheral nervous system and other types of tumour, such as melanoma, sarcoma, fibrosarcoma and osteosarcoma. The compounds according to the invention are also suitable for the treatment of other proliferative diseases. The compounds according to the invention can also be used in combination with a broad range of DNA-damaging agents, but can also be used as individual substance.

The present invention therefore relates to the use of the compounds according to the invention for the treatment of diseases or conditions in which inhibition of CHK1 and/or CHK2 activity is advantageous.

Like CHK1 and CHK2, SGK belongs to the serine/threonine kinases.

The present invention furthermore relates to the use of the compounds according to the invention, where the inhibition, regulation and/or modulation of signal transduction of the cell volume-regulated human kinase H-SGK (human serum and glucocorticoid dependent kinase or SGK) plays a role, for the treatment of SGK-induced diseases.

SGKs with the isoforms SGK-1, SGK-2 and SGK-3 are a serine/threonine protein kinase family (WO 02/17893).

The compounds according to the invention are inhibitors of SGK-1. They may furthermore be inhibitors of SGK-2 and/or SGK-3.

The present invention thus relates to the use of the compounds according to the invention which inhibit, regulate and/or modulate SGK signal transduction, to compositions which comprise these compounds, and to processes for the use thereof for the treatment of SGK-induced diseases and complaints, such as diabetes (for example diabetes mellitus, diabetic nephropathy, diabetic neuropathy, diabetic angiopathy and microangiopathy), obesity, metabolic syndrome (dyslipidaemia), systemic and pulmonary hypertonia, cardiovascular diseases (for example cardiac fibroses after myocardial infarction, cardiac hypertrophy and cardiac insufficiency, arteriosclerosis) and renal diseases (for example glomerulosclerosis, nephrosclerosis, nephritis, nephropathy, electrolyte excretion disorder), generally in fibroses and inflammatory processes of any type (for example liver cirrhosis, pulmonary fibrosis, fibrosing pancreatitis, rheumatism and arthroses, Crohn's disease, chronic bronchitis, radiation fibrosis, sclerodermatitis, cystic fibrosis, scarring, Alzheimer's disease).

The compounds according to the invention can also inhibit the growth of tumour cells and tumour metastases and are therefore suitable for tumour therapy.

The compounds according to the invention are furthermore used for the treatment of coagulopathies, such as, for example, dysfibrinogenaemia, hypoproconvertinaemia, haemophilia B, Stuart-Prower defect, prothrombin complex deficiency, consumption coagulopathy, hyperfibrinolysis, immuno-coagulopathy or complex coagulopathies, and also in neuronal excitability, for example epilepsy. The compounds according to the invention can also be employed therapeutically in the treatment of glaucoma or a cataract. The compounds according to the invention are furthermore used in the treatment of bacterial infections and in anti-infection therapy. The compounds according to the invention can also be employed therapeutically for increasing learning ability and attention. In addition, the compounds according to the invention counter cell ageing and stress and thus increase life expectancy and fitness in the elderly.

The compounds according to the invention are furthermore used in the treatment of tinnitus.

The identification of small compounds which inhibit, regulate and/or modulate SGK signal transduction is therefore desirable and an aim of the present invention.

It has been found that the compounds according to the invention and salts thereof have very valuable pharmacological properties while being well tolerated.

Thus, they also exhibit SGK-inhibiting properties.

The present invention therefore relates to compounds according to the invention as medicaments and/or medicament active ingredients in the treatment and/or prophylaxis of the said diseases and to the use of compounds according to the invention for the preparation of a pharmaceutical for the treatment and/or prophylaxis of the said diseases and also to a process for the treatment of the said diseases which comprises the administration of one or more compounds according to the invention to a patient in need of such an administration.

The host or patient may belong to any mammal species, for example a primate species, particularly humans; rodents, including mice, rats and hamsters; rabbits; horses, cows, dogs, cats, etc. Animal models are of interest for experimental investigations, where they provide a model for the treatment of a human disease.

For identification of a signal transduction pathway and for detection of interactions between various signal transduction pathways, various scientists have developed suitable models or model systems, for example cell culture models (for example Khwaja et al., EMBO, 1997, 16, 2783-93) and models of transgenic animals (for example White et al., Oncogene, 2001, 20, 7064-7072). For the determination of certain stages in the signal transduction cascade, interacting compounds can be utilised in order to modulate the signal (for example Stephens et al., Biochemical J., 2000, 351, 95-105). The compounds according to the invention can also be used as reagents for testing kinase-dependent signal transduction pathways in animals and/or cell culture models or in the clinical diseases mentioned in this application.

Measurement of the kinase activity is a technique which is well known to the person skilled in the art. Generic test systems for the determination of the kinase activity using substrates, for example histone (for example Alessi et al., FEBS Lett. 1996, 399, 3, pages 333-338) or the basic myelin protein, are described in the literature (for example Campos-González, R. and Glenney, Jr., J. R. 1992, J. Biol. Chem. 267, page 14535).

Various assay systems are available for identification of kinase inhibitors. In the scintillation proximity assay (Sorg et al., J. of. Biomolecular Screening, 2002, 7, 11-19) and the flashplate assay, the radioactive phosphorylation of a protein or peptide as substrate is measured using γATP. In the presence of an inhibitory compound, a reduced radioactive signal, or none at all, can be detected. Furthermore, homogeneous time-resolved fluorescence resonance energy transfer (HTR-FRET) and fluorescence polarisation (FP) technologies are useful as assay methods (Sills et al., J. of Biomolecular Screening, 2002, 191-214).

Other non-radioactive ELISA assay methods use specific phospho antibodies (phospho ABs). The phospho AB only binds the phosphorylated substrate. This binding can be detected by chemoluminescence using a second peroxidase-conjugated antisheep antibody (Ross et al., Biochem. J., 2002, 366, 977-981).

PRIOR ART

Other indazole derivatives are described as protein kinase inhibitors in WO 03/064397.

In Bioorganic & Medicinal Chemistry Letters 13 (2003) 3059-3062, J. Witherington et al. the preparation of other indazole derivatives.

Other indazole derivatives are described as kinase inhibitors in WO 2003097610.

Other indazole derivatives are disclosed as GSK-3 inhibitors in WO 2003051847.

The preparation of indazole compounds which act as Rho kinase inhibitors is known from WO 2005035506.

The preparation of aminoindazoles which act as protein tau phosphorylation inhibitors is disclosed in WO 2004062662, FR 2848554, WO 2004022544 and FR 2844267.

WO 00/62781 describes the use of medicaments comprising inhibitors of cell volume-regulated human kinase H-SGK.

The use of kinase inhibitors in antiinfection therapy is described by C. Doerig in Cell. Mol. Biol. Lett. Vol. 8, No. 2A, 2003, 524-525.

The use of kinase inhibitors in obesity is described by N. Perrotti in J. Biol. Chem. 2001, March 23; 276(12):9406-9412.

The following references suggest and/or describe the use of SGK inhibitors in disease treatment:

1: Chung E J, Sung Y K, Farooq M, Kim Y, Im S, Tak W Y, Hwang Y J, Kim Y I, Han H S, Kim J C, Kim M K. Gene expression profile analysis in human hepatocellular carcinoma by cDNA microarray. Mol. Cells. 2002; 14:382-7.

2: Brickley D R, Mikosz C A, Hagan C R, Conzen S D. Ubiquitin modification of serum and glucocorticoid-induced protein kinase-1(SGK-1). J Biol. Chem. 2002; 277:43064-70.

3: Fillon S, Klingel K, Warntges S, Sauter M, Gabrysch S, Pestel S, Tanneur V, Waldegger S, Zipfel A, Viebahn R, Haussinger D, Broer S, Kandolf R, Lang F. Expression of the serine/threonine kinase hSGK1 in chronic viral hepatitis. Cell Physiol Biochem. 2002; 12:47-54.

4: Brunet A, Park J, Tran H, Hu L S, Hemmings B A, Greenberg M E. Protein kinase SGK mediates survival signals by phosphorylating the forkhead transcription factor FKHRL1 (FOXO3a). Mol Cell Biol 2001; 21:952-65

5: Mikosz C A, Brickley D R, Sharkey M S, Moran T W, Conzen S D. Glucocorticoid receptor-mediated protection from apoptosis is associated with induction of the serine/threonine survival kinase gene, sgk-1. J Biol. Chem. 2001; 276:16649-54.

6: Zuo Z, Urban G, Scammell J G, Dean N M, McLean T K, Aragon I, Honkanen R E. Ser/Thr protein phosphatase type 5 (PP5) is a negative regulator of glucocorticoid receptor-mediated growth arrest. Biochemistry. 1999; 38:8849-57.

7: Buse P, Tran S H, Luther E, Phu P T, Aponte G W, Firestone G L. Cell cycle and hormonal control of nuclear-cytoplasmic localisation of the serum- and glucocorticoid-inducible protein kinase, Sgk, in mammary tumour cells. A novel convergence point of anti-proliferative and proliferative cell signalling pathways. J Biol. Chem. 1999; 274:7253-63.

8: M. Hertweck, C. Göbel, R. Baumeister: *C. elegans* SGK-1 is the critical component in the Akt/PKB Kinase complex to control stress response and life span. Developmental Cell, Vol. 6, 577-588, April, 2004.

SUMMARY OF THE INVENTION

The invention relates to compounds selected from the group

| No. | Chemical structure Name | Retention time Rf [min] | HPLC method |
|---|---|---|---|
| "A1" | 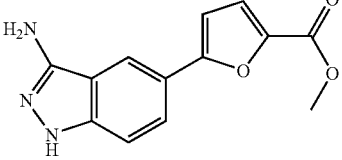<br>Methyl 5-(3-amino-1H-indazol-5-yl)furan-2-carboxylate | 0.98 | A |
| "A2" | 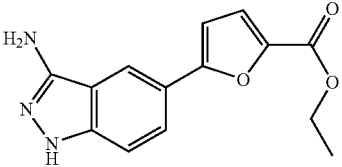<br>Methyl 5-(3-amino-1H-indazol-5-yl)furan-2-carboxylate | 1.163 | A |
| "A2a" | 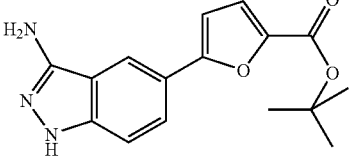<br>tert-Butyl 5-(3-amino-1H-indazol-5-yl)furan-2-carboxylate | | |
| "A3" | 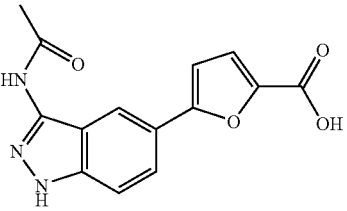<br>5-(3-Acetylamino-1H-indazol-5-yl)furan-2-carboxylic acid | | |
| "A4" | 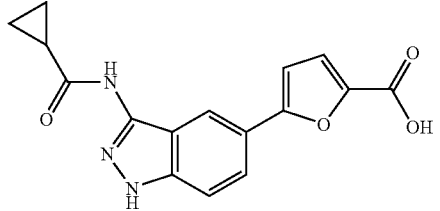<br>5-[3-(Cyclopropanecarbonylamino)-1H-indazol-5-yl]furan-2-carboxylic acid | 0.927 | A |

-continued

| No. | Chemical structure Name | Retention time Rf [min] | HPLC method |
|---|---|---|---|
| "A5" | 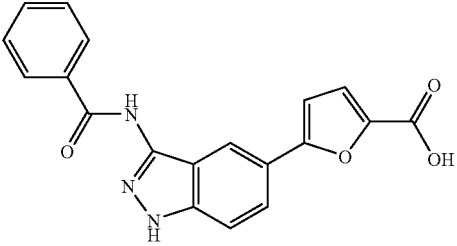<br>5-(3-Benzoylamino-1H-indazol-5-yl)furan-2-carboxylic acid | | |
| "A6" | 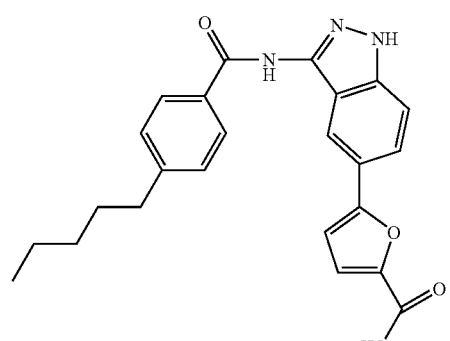<br>5-[3-(4-Pentylbenzoylamino)-1H-indazol-5-yl]furan-2-carboxylic acid | 1.791 | A |
| "A7" | 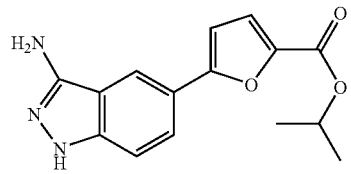<br>Isopropyl 5-(3-amino-1H-indazol-5-yl)furan-2-carboxylate | 1.284 | A |
| "A8" | 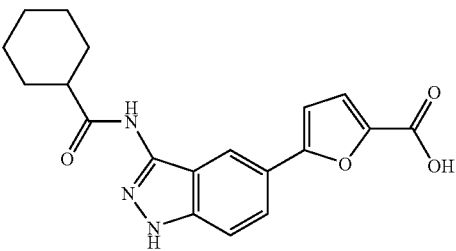<br>5-[3-(Cyclohexanecarbonylamino)-1H-indazol-5-yl]furan-2-carboxylic acid | 1.306 | A |
| "A9" | 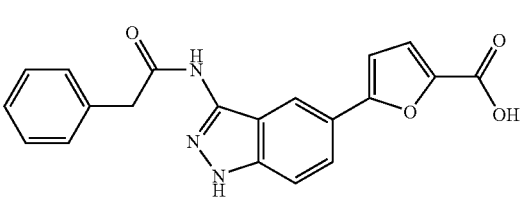<br>5-(3-Phenylacetylamino-1H-indazol-5-yl)-furan-2-carboxylic acid | 1.237 | A |

-continued

| No. | Chemical structure Name | Retention time Rf [min] | HPLC method |
|---|---|---|---|
| "A10" | 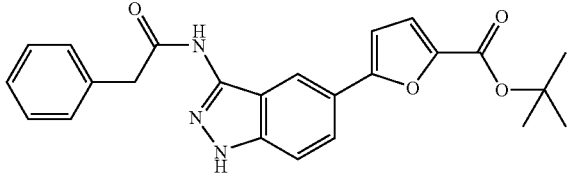<br>5-(3-Phenylacetylamino-1H-indazol-5-yl)-furan-2-carboxylic acid | 2.231 | A |
| "A11" | 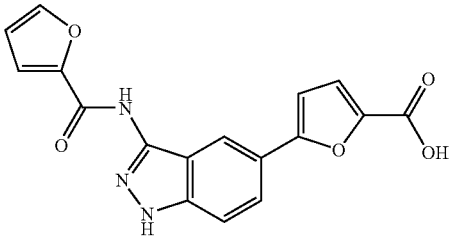<br>5-{3-[(Furan-2-carbonyl)amino]-1H-indazol-5-yl}furan-2-carboxylic acid | 1.543 | A |
| "A12" | 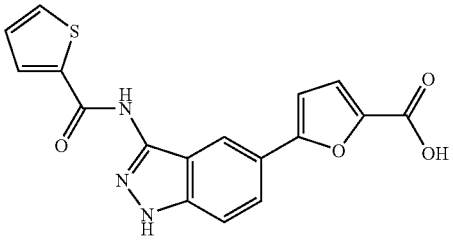<br>5-{3-[(Thiophene-2-carbonyl)amino]-1H-indazol-5-yl}furan-2-carboxylic acid | 1.639 | A |
| "A13" | 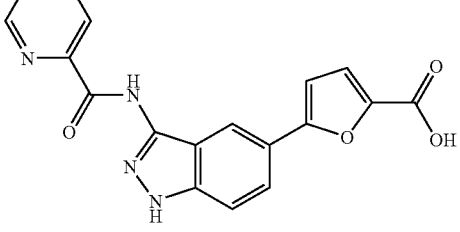<br>5-{3-[(Pyridine-2-carbonyl)amino]-1H-indazol-5-yl}furan-2-carboxylic acid | 1.653 | A |
| "A14" | 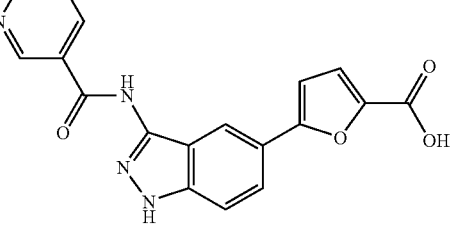<br>5-{3-[(Pyridine-3-carbonyl)amino]-1H-indazol-5-yl}furan-2-carboxylic acid | 1.333 | A |

-continued
| No. | Chemical structure<br>Name | Retention time<br>Rf [min] | HPLC<br>method |
|---|---|---|---|
| "A15" | 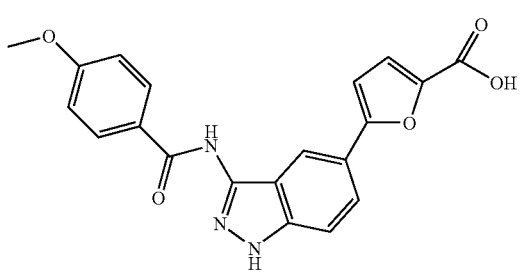<br>5-[3-(4-Methoxybenzoylamino)-1H-indazol-5-yl]furan-2-carboxylic acid | 1.712 | A |
| "A16" | 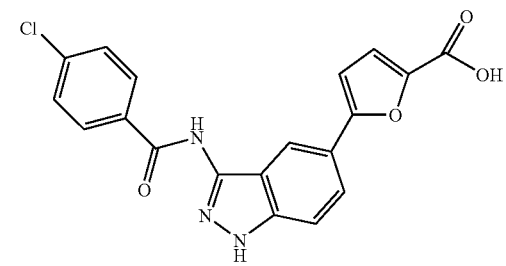<br>5-[3-(4-Chlorobenzoylamino)-1H-indazol-5-yl]furan-2-carboxylic acid | 1.837 | A |
| "A17" | 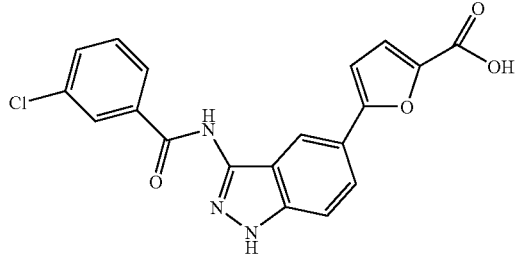<br>5-[3-(3-Chlorobenzoylamino)-1H-indazol-5-yl]furan-2-carboxylic acid | 1.842 | A |
| "A18" | 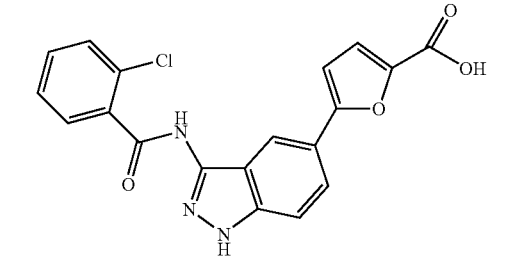<br>5-[3-(2-Chlorobenzoylamino)-1H-indazol-5-yl]furan-2-carboxylic acid | 1.703 | A |

-continued
| No. | Chemical structure Name | Retention time Rf [min] | HPLC method |
|---|---|---|---|
| "A19" | 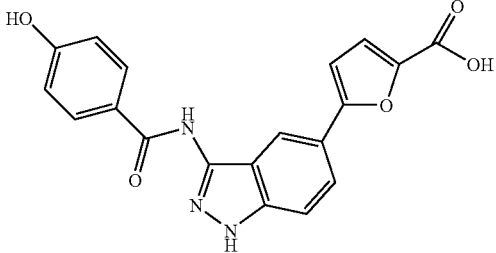<br>5-[3-(4-Hydroxybenzoylamino)-1H-indazol-5-yl]furan-2-carboxylic acid | 1.534 | A |
| "A20" | 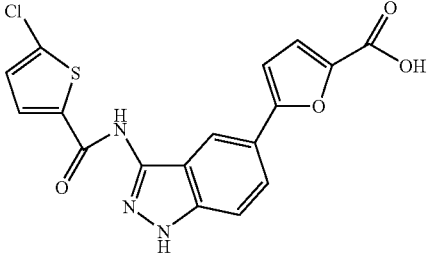<br>5-{3-[(5-Chlorothiophene-2-carbonyl)amino]-1H-indazol-5-yl}furan-2-carboxylic acid | 1.767 | A |
| "A21" | 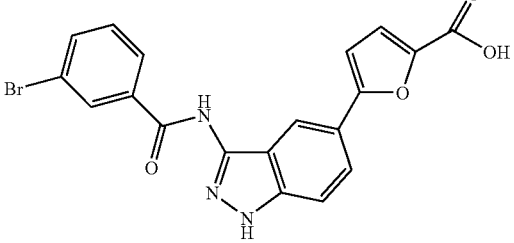<br>5-[3-(3-Bromobenzoylamino)-1H-indazol-5-yl]furan-2-carboxylic acid | 1.779 | A |
| "A22" | 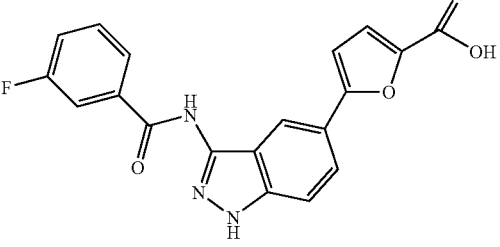<br>5-[3-(3-Fluorobenzoylamino)-1H-indazol-5-yl]furan-2-carboxylic acid | 1.655 | A |

-continued
| No. | Chemical structure Name | Retention time Rf [min] | HPLC method |
|---|---|---|---|
| "A23" | 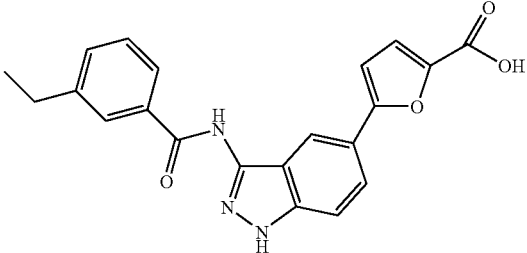<br>5-[3-(3-Ethylbenzoylamino)-1H-indazol-5-yl]-furan-2-carboxylic acid | 1.806 | A |
| "A24" | 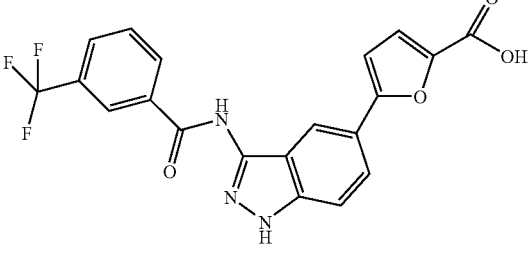<br>5-[3-(3-Trifluoromethylbenzoylamino)-1H-indazol-5-yl]furan-2-carboxylic acid | 1.834 | A |
| "A25" | 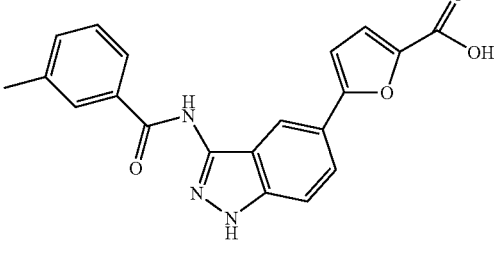<br>5-[3-(3-Methylbenzoylamino)-1H-indazol-5-yl]furan-2-carboxylic acid | 1.702 | A |
| "A26" | 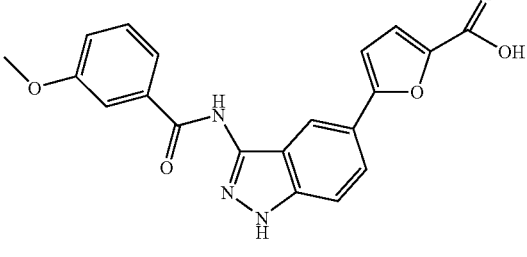<br>5-[3-(3-Methoxybenzoylamino)-1H-indazol-5-yl]furan-2-carboxylic acid | 1.636 | A |

-continued

| No. | Chemical structure Name | Retention time Rf [min] | HPLC method |
|---|---|---|---|
| "A27" | 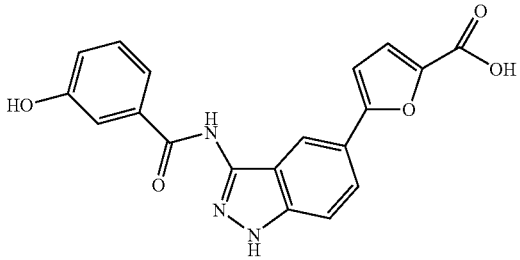<br>5-[3-(3-Hydroxybenzoylamino)-1H-indazol-5-yl]furan-2-carboxylic acid | 1.455 | A |
| "A28" | 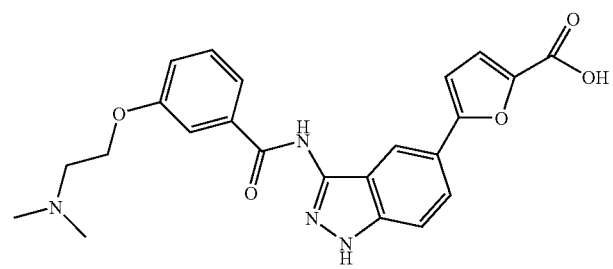<br>5-{3-[3-(2-Dimethylaminoethoxy)benzoyl-amino]-1H-indazol-5-yl}furan-2-carboxylic acid | 1.482 | A | and pharmaceutically usable derivatives, solvates, salts, tautomers and stereoisomers thereof, including mixtures thereof in all ratios.

The invention also relates to the optically active forms (stereoisomers), the enantiomers, the racemates, the diastereomers, and the hydrates and solvates of these compounds. Solvate of the compounds are taken to mean adductions of inert solvent molecules onto the compounds which form owing to their mutual attractive force. Solvate are, for example, mono- or dihydrates or alcoholates.

Pharmaceutically usable derivatives are taken to mean, for example, the salts of the compounds according to the invention and also so-called pro-drug compounds.

Prodrug derivatives are taken to mean compounds of the formula I which have been modified with, for example, alkyl or acyl groups, sugars or oligopeptides and which are rapidly cleaved in the organism to form the active compounds according to the invention.

These also include biodegradable polymer derivatives of the compounds according to the invention, as is described, for example, in Int. J. Pharm. 115, 61-67 (1995).

The expression "effective amount" means the amount of a medicament or pharmaceutical active ingredient which causes a biological or medical response which is sought or aimed at, for example by a researcher or physician, in a tissue, system, animal or human.

In addition, the expression "therapeutically effective amount" means an amount which, compared with a corresponding subject who has not received this amount, has the following consequence: improved treatment, healing, prevention or elimination of a disease, syndrome, condition, complaint, disorder or side effects or also the reduction in the progress of a disease, complaint or disorder.

The expression "therapeutically effective amount" also encompasses the amounts which are effective for increasing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

The compounds according to the invention and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use may also be made here of variants known per se which are not mentioned here in greater detail.

If desired, the starting materials can also be formed in situ by not isolating them from the reaction mixture, but instead immediately converting them further into the compounds of the formula I.

The compounds according to the invention can preferably be obtained by reacting compounds of the formula II

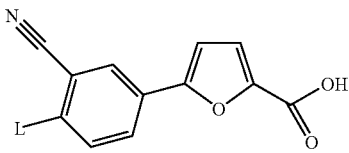

with hydrazine, and subsequently, if desired, esterifying the product (for example analogously to Synthesis Scheme 1).

Synthesis Scheme 1:

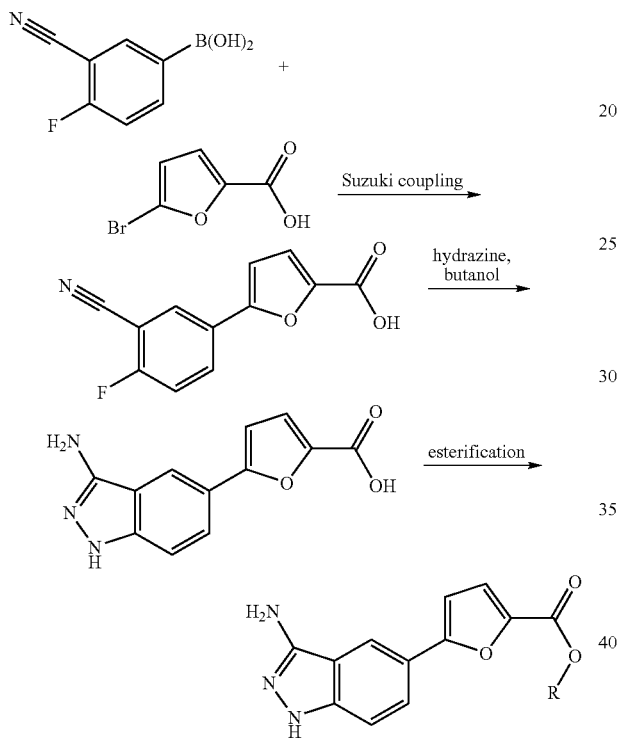

In the compounds of the formula II, L preferably denotes F, Cl, Br, I or a free or a reactively modified OH group, such as, for example, an activated ester, an imidazolide or alkylsulfonyloxy having 1-6 C atoms (preferably methylsulfonyloxy or trifluoromethylsulfonyloxy) or arylsulfonyloxy having 6-10 C atoms (preferably phenyl- or p-tolylsulfonyloxy). In the compounds of the formula II, L preferably denotes F.

The reaction is generally carried out in an inert solvent. Depending on the conditions used, the reaction time is between a few minutes and 14 days, the reaction temperature is between about 0° and 150°, normally between 15° and 120°, particularly preferably between 50 and 100° C.

Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as aceta-mide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents, butanol is particularly preferred.

Compounds of the formula I can furthermore be obtained by reacting compounds of the formula III

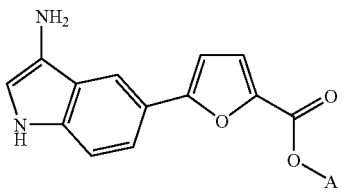

in which A denotes alkyl having 1, 2, 3, 4, 5 or 6 C atoms, with compounds of the formula IV

R—CO-L                    IV in which R preferably denotes methyl, ethyl, propyl, butyl, pentyl, hexyl, cyclopropyl, cyclobutyl, cyclopentyl, cyclohexyl, phenyl, benzyl, furyl, thienyl, pyridyl, o-, m- or p-methoxyphenyl, o-, m- or p-chlorophenyl, o-, m- or p-hydroxyphenyl, o-, m- or p-bromophenyl, o-, m- or p-fluorophenyl, o-, m- or p-methylphenyl, o-, m- or p-ethylphenyl, o-, m- or p-trifluoromethyl-phenyl, o-, m- or p-(2-dimethylaminoethoxy)phenyl, and subsequently cleaving the ester (for example analogously to Synthesis Scheme 2).

Synthesis Scheme 2:

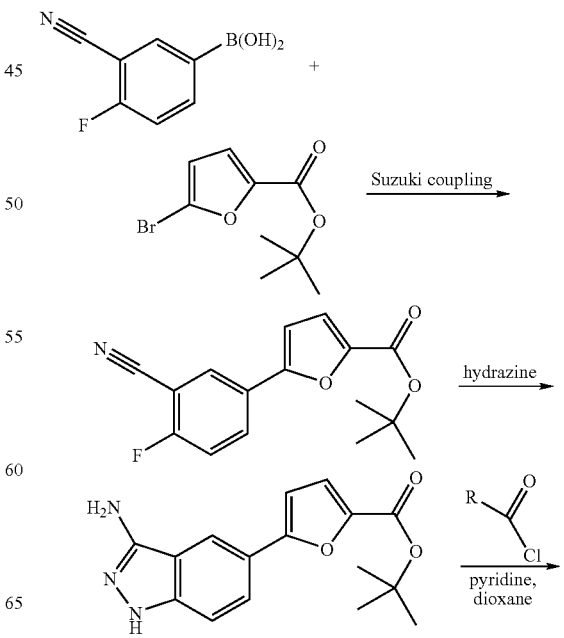

-continued

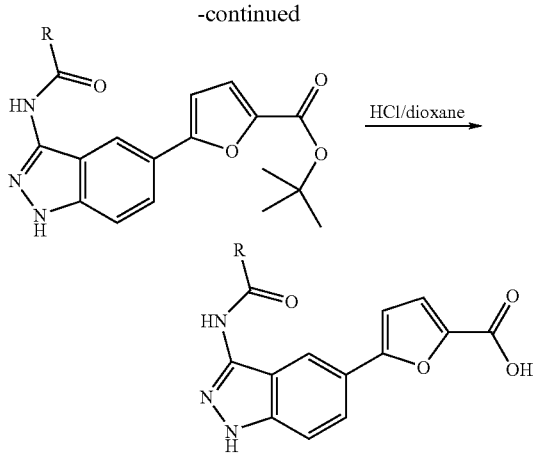

In the compounds of the formula IV, L preferably denotes F, Cl, Br, I or a free or a reactively modified OH group, such as, for example, an activated ester, an imidazolide or alkylsulfonyloxy having 1-6 C atoms (preferably methylsulfonyloxy or trifluoromethylsulfonyloxy) or arylsulfonyloxy having 6-10 C atoms (preferably phenyl- or p-tolylsulfonyloxy). In the compounds of the formula IV, L preferably denotes Cl.

Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart).

Activated esters are advantageously formed in situ, for example by addition of HOBt, N-hydroxysuccinimide or DAPECI (N-(3-dimethylamino-propyl)-N-ethylcarbodiimide hydrochloride).

The reaction is generally carried out in an inert solvent. Depending on the conditions used, the reaction time is between a few minutes and 14 days, the reaction temperature is between about 0° and 150°, normally between 15° and 120°, particularly preferably between 20 and 100° C.

Suitable inert solvents are those mentioned above, DMF is preferred.

The reaction is optionally carried out in the presence of an acid-binding agent, preferably an alkali-metal or alkaline-earth metal hydroxide, carbonate or bicarbonate or another salt of a weak acid of the alkali metals or alkaline-earth metals, preferably of potassium, sodium, calcium or caesium. The addition of an organic base, such as triethylamine, dimethylaniline, pyridine or quinoline or an excess of the amine component of the formula IV may be favourable. Depending on the conditions used, the reaction time is between a few minutes and 14 days, the reaction temperature is between about 0° and 150°, normally between 15° and 120°, particularly preferably between 20 and 130° C.

Suitable inert solvents are those mentioned above.

The ester cleavage is carried out under standard conditions, as known to the person skilled in the art.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds according to the invention are for the most part prepared by conventional methods. If the compound according to the invention contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline-earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds according to the invention are likewise included. In the case of certain compounds according to the invention, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluorooacetate, tartrate, maleate, succinate, citrate, benzoate, salicylate, ascorbate and the like. Accordingly, pharmaceutically acceptable acid-addition salts of the compounds according to the invention include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline-earth metal salts calcium and magnesium. Salts of the compounds according to the invention which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine(benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromoine, triethanolamine, triethylamine, tripropylamine and tris(hydroxymethyl)methylamine(tromethamine), but this is not intended to represent a restriction.

Compounds of the present invention which contain basic nitrogen-containing groups can be quaternised using agents such as $(C_1-C_4)$alkyl halides, for example methyl, ethyl, isopropyl and tert-butyl chloride, bromide and iodide; di$(C_1-C_4)$ alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl$(C_1-C_4)$alkyl halides, for example benzyl chloride and phenethyl bromide. Both water- and oil-soluble compounds according to the invention can be prepared using such salts.

The above-mentioned pharmaceutical salts which are preferred include acetate, trifluorooacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds according to the invention are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds according to the invention are formed with metals or amines, such as alkali metals and alkaline-earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound according to the invention in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The invention furthermore relates to medicaments comprising at least one compound according to the invention and/or pharmaceutically usable derivatives, solvates and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an ab-sorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds according to the invention and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds according to the invention and the salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodoegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanooacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound according to the invention depends on a number of factors, including, for example, the age and weight of the animal, the precise condition which requires treatment, and its severity, the nature of the formulation and the method of administration, and is ultimately determined by the treating doctor or vet. However, an effective amount of a compound according to the invention for the treatment of neoplastic growth, for example large bowel or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or more usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least one compound according to the invention and/or pharmaceutically usable derivatives, solvates and stereoisomers thereof, including mixtures thereof in all ratios, and at least one further medicament active ingredient.

The invention also relates to a set (kit) consisting of separate packs of
(a) an effective amount of a compound according to the invention and/or pharmaceutically usable derivatives, solvates and stereoisomers thereof, including mixtures thereof in all ratios, and
(b) an effective amount of a further medicament active ingredient.

The set comprises suitable containers, such as boxes, individual bottles, bags or ampoules. The set may, for example, comprise separate ampoules, each containing an effective amount of a compound according to the invention and/or pharmaceutically usable derivatives, solvates and stereoisomers thereof, including mixtures thereof in all ratios, and an effective amount of a further medicament active ingredient in dissolved or lyophilised form.

Use

1. The disclosed compounds according to the invention are particularly useful in therapeutic applications relating to a CHK1-mediated disorder. As used herein, the term "CHK-1-mediated disorder" encompasses any disorder, disease or condition which is caused or characterised by an increase in CHK1 expression or activity, or which requires CHK1 activity. The term "CHK1-mediated disorder" also encompasses any disorder, disease or condition in which inhibition of CHK1 activity is beneficial.

CHK1 inhibition can be used to achieve a beneficial therapeutic or prophylactic effect, for example in patients having a proliferative disorder. Non-limiting examples of proliferative disorders include chronic inflammatory proliferative disorders, for example psoriasis and rheumatoid arthritis, proliferative ocular disorders, for example diabetic retinopathy, benign proliferative disorders, for example haemangiomas, and cancer. As used herein, the term "cancer" relates to a cellular disorder characterised by uncontrolled or disregulated cell proliferation, decreased cell differentiation, inappropriate ability to invade surrounding tissue, and/or ability to establish new growth at ectopic sites. The term "cancer" encompasses, but is not limited to, solid tumours and blood-borne tumours. The term "cancer," encompasses diseases of skin, tissues, organs, bone, cartilage, blood and vessels. The term "cancer" furthermore encompasses primary and metastatic cancer diseases.

Non-limiting examples of solid tumours that can be treated with the disclosed CHK1 inhibitors include pancreatic cancer, bladder cancer, colorectal cancer, breast cancer, including metastatic breast cancer, prostate cancer, including androgen-dependent and androgen-independent prostate cancer, renal cancer, including, for example, metastatic renal-cell carcinoma, hepatocellular cancer, lung cancer, including, for example, non-small-cell lung cancer (NSCLC), bronchioloalveolar carcinoma (BAC), and adenocrarcinoma of the lung, ovarian cancer, including, for example, progressive epithelial or primary peritoneal cancer, cervical cancer, gastric cancer, oesophageal cancer, head and neck cancer, including, for example, squamous cell carcinoma of the head and neck, melanoma, neuro endocrine cancer, including metastatic neuroendocrine tumours, brain tumours, including for example, glioma, anaplastic oligodendroglioma, adult glioblastoma multiforme, and adult anaplastic astrocytoma, bone cancer and soft tissue sarcoma.

Nonlimiting examples of haemiatological malignancies that can be treated with the disclosed CHK1 inhibitors include acute myeloid leukaemia (AML), chronic myeloid leukaemia (CML), including accelerated CML and CML blast phase (CML-BP), acute lymphoblastic leukaemia (ALL), chronic lymphocytic leukaemia (CLL), Hodgkin's disease (HD), non-Hodgkin's lymphoma (NHL), including follicular lymphoma and mantle cell lymphoma, B-cell lymphoma, T-cell lymphoma, multiple myeloma (MM), Waldenström's macroglobulinaemia, myelodysplastic syndromes (MDS), including refractory anaemia (RA), refractory anaemia with ringed sideoblasts (RARS), refractory anaemia with excess blasts (RAEB), and RAEB in transformation (RAEB-T), and myeloproliferative syndromes.

The disclosed compounds according to the invention are particularly suitable for the treatment of cancers or cell types in which CHK1 protein or activity is upregulated, including, without limitation, rapidly proliferating cells and drug-resistant cells (Shyjan et al, U.S. Pat. No. 6,723,498 (2004)), as well as retinoblastomas, such as Rb-negative or inactivated cells (Gottifredi et al., Mol. Cell. Biol., 21:1066 (2001)) or in which the ARF$^{p14/p19}$ locus has been inactivated or misregulated. The disclosed CHK1 inhibitors also are particularly suitable for the treatment of cancer types or cell types in which another checkpoint pathway has been mutated or abrogated, including, without limitation, cancers types or cell types in which p53 or the p53 pathway has been inactivated or abrogated.

The disclosed compounds according to the invention can be administered in combination with other therapeutic agents, including anticancer agents. As used herein, the term "anticancer agent" relates to any agent which is administered to a patient with cancer for the purposes of treating the cancer.

The anti-cancer treatment defined herein may be applied as a sole therapy or may involve, in addition to the compound of the invention, conventional surgery or radiotherapy or chemotherapy. Such chemotherapy may include one or more of the following categories of anti-tumour agents:

(i) antiproliferative/antineoplastic/DNA-damaging agents and combinations thereof, as used in medical oncology, such as alkylating agents (for example cis-platin, carboplatin, cyclophosphamide, nitrogen mustard, melphalan, chloroambucil, busulphan and nitrosoureas); antimetabolites (for example antifolates such as fluoroopyrimidines like 5-fluoroouracil and tegafur, raltitrexed, methotrexate, cytosine arabinoside, hydroxyurea and gemcitabine); antitumour antibiotics (for example anthracyclines, like adriamycin, bleomycin, doxorubicin, daunomycin, epirubicin, idarubicin, mito-mycin-C, dactinomycin and mithramycin); antimitotic agents (for example vinca alkaloids, like vincristine, vinblastine, vindesine and vinorelbine, and taxoids, like taxol and taxotere); topoisomerase inhibitors (for example epipodophyllotoxins, like etoposide and teniposide, amsacrine, topotecan, irinotecan and camptothecin) and cell-differentiating agents (for example all-trans-retinoic acid, 13-cis-retinoic acid and fenretinide);

(ii) cytostatic agents, such as antioestrogens (for example tamoxifen, toremifene, raloxifene, droloxifene and iodooxyfene), oestrogen receptor downregulators (for example fulvestrant), antiandrogens (for example bi-calutamide, flutamide, nilutamide and cyproterone acetate), LHRH antagonists or LHRH agonists (for example goserelin, leuprorelin and buserelin), progesterones (for example megestrol acetate), aromatase inhibitors (for example as anastrozole, letrozole, vorazole and exemestane) and inhibi-tors of 5α-reductase, such as finasteride;

(iii) agents which inhibit cancer cell invasion (for example metalloproteinase inhibitors, like marimastat, and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors, such as N-(3-chloro-4-fluoroophenyl)-7-methoxy-6-(3-morpholino propoxy) quinazolin-4-amine(gefitinib, AZD1839), N-(3-ethynylphenyl)-6,7-bis(2-methoxyethoxy)quinazolin-4-amine(erlotinib, OSI-774) and 6-acrylamido-N-(3-chloro-4-fluoroophenyl)-7-(3-morpholino-propoxy) quinazolin-4-amine(Cl11033)), for example inhibitors of the platelet-derived growth factor family and for example inhibitors of the hepatocyte growth factor family;

(v) antiangiogenic agents, such as those which inhibit the effects of vascular endothelial growth factor, (for example the anti-vascular endothelial cell growth factor antibody bevacizumab [Avastin™], compounds such as those disclosed in published international patent applications WO 97/22596, WO 97/30035, WO 97/32856 and WO 98/13354) and compounds that work by other mechanisms (for example linomide, inhibitors of integrin αvβ3 function and angiostatin);

(vi) vessel-damaging agents, such as combretastatin A4 and compounds disclosed in international patent applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-Ras antisense;

(viii) gene therapy approaches, including, for example, approaches for replacement of aberrant genes, such as aberrant p53 or aberrant BRCA1 or BRCA2, GDEPT (gene-directed enzyme pro-drug therapy) approaches, such as those using cytosine deaminase, thymidine kinase or a bacterial nitroreductase enzyme, and approaches for increasing patient tolerance to chemotherapy or radiotherapy, such as multi-drug resistance gene therapy; and (ix) immunotherapy approaches, including, for example, ex-vivo and in-vivo approaches for increasing the immunogenicity of patient tumour cells, such as transfection with cytokines, such as interleukin 2, interleukin 4 or granulocyte-macrophage colony stimulating factor, approaches for decreasing T-cell anergy, approaches using transfected immune cells, such as cytokine-transfected dendritic cells, approaches using cytokine-transfected tumour cell lines, and approaches using anti-idiotypic antibodies.

The medicaments from Table 1 below are preferably, but not exclusively, combined with the compounds according to the invention.

TABLE 1

| | | |
|---|---|---|
| Alkylating agents | Cyclophosphamide | Lomustine |
| | Busulfan | Procarbazine |
| | Ifosfamide | Altretamine |
| | Melphalan | Estramustine phosphate |
| | Hexamethylmelamine | Mechloroethamine |
| | Thiotepa | Streptozocin |
| | chloroambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (Aetema) |
| | Carboxyphthalatoplatinum | Satraplatin (Johnson Matthey) |
| | Tetraplatin | |
| | Ormiplatin | BBR-3464 |
| | Iproplatin | (Hoffmann-La Roche) |
| | | SM-11355 (Sumitomo) |
| | | AP-5280 (Access) |
| Antimetabolites | Azacytidine | Tomudex |
| | Gemcitabine | Trimetrexate |
| | Capecitabine | Deoxycoformycin |
| | 5-fluoroouracil | Fludarabine |
| | Floxuridine | Pentostatin |
| | 2-chlorodesoxyadenosine | Raltitrexed |

TABLE 1-continued

| | | |
|---|---|---|
| | 6-Mercaptopurine | Hydroxyurea |
| | 6-Thioguanine | Decitabine (SuperGen) |
| | Cytarabine | Clofarabine (Bioenvision) |
| | 2-fluoroodesoxycytidine | Irofulven (MGI Pharma) |
| | Methotrexate | DMDC (Hoffmann-La Roche) |
| | Idatrexate | Ethynylcytidine (Taiho) |
| Topoisomerase inhibitors | Amsacrine | Rubitecan (SuperGen) |
| | Epirubicin | Exatecan mesylate (Daiichi) |
| | Etoposide | Quinamed (ChemGenex) |
| | Teniposide or mitoxantrone | Gimatecan (Sigma-Tau) |
| | Irinotecan (CPT-11) | Diflomotecan (Beaufour-Ipsen) |
| | 7-Ethyl-10-hydroxycamptothecin | TAS-103 (Taiho) |
| | Topotecan | Elsamitrucin (Spectrum) |
| | Dexrazoxanet (TopoTarget) | J-107088 (Merck & Co) |
| | Pixantrone (Novuspharrna) | BNP-1350 (BioNumerik) |
| | Rebeccamycin analogue (Exelixis) | CKD-602 (Chong Kun Dang) |
| | BBR-3576 (Novuspharrna) | KW-2170 (Kyowa Hakko) |
| Antitumour antibiotics | Dactinomycin (Actinomycin D) | Amonafide |
| | | Azonafide |
| | Doxorubicin (Adriamycin) | Anthrapyrazole |
| | Deoxyrubicin | Oxantrazole |
| | Valrubicin | Losoxantrone |
| | Daunorubicin (Daunomycin) | Bleomycin sulfate (Blenoxan) |
| | Epirubicin | Bleomycinic acid |
| | Therarubicin | Bleomycin A |
| | Idarubicin | Bleomycin B |
| | Rubidazon | Mitomycin C |
| | Plicamycinp | MEN-10755 (Menarini) |
| | Porfiromycin | GPX-100 (Gem Pharmaceuticals) |
| | Cyanoomorpholinodoxorubicin | |
| | Mitoxantron (Novantron) | |
| Antimitotic agents | Paclitaxel | SB 408075 (GlaxoSmithKline) |
| | Docetaxel | E7010 (Abbott) |
| | Colchicine | PG-TXL (Cell Therapeutics) |
| | Vinblastine | |
| | Vincristine | IDN 5109 (Bayer) |
| | Vinorelbine | A 105972 (Abbott) |
| | Vindesine | A 204197 (Abbott) |
| | Dolastatin 10 (NCI) | LU 223651 (BASF) |
| | Rhizoxin (Fujisawa) | D 24851 (ASTA Medica) |
| | Mivobulin (Warner-Lambert) | ER-86526 (Eisai) |
| | Cemadotin (BASF) | Combretastatin A4 (BMS) |
| | RPR 109881A (Aventis) | Isohomohalichondrin-B (PharmaMar) |
| | TXD 258 (Aventis) | ZD 6126 (AstraZeneca) |
| | Epothilone B (Novartis) | PEG-Paclitaxel (Enzon) |
| | T 900607 (Tularik) | AZ10992 (Asahi) |
| | T 138067 (Tularik) | !DN-5109 (Indena) |
| | Cryptophycin 52 (Eli Lilly) | AVLB (Prescient NeuroPharma) |
| | Vinflunine (Fabre) | |
| | Auristatin PE (Teikoku Hormone) | Azaepothilon B (BMS) |
| | BMS 247550 (BMS) | BNP-7787 (BioNumerik) |
| | BMS 184476 (BMS) | CA-4-Prodrug (OXiGENE) |
| | BMS 188797 (BMS) | Dolastatin-10 (NrH) |
| | Taxoprexin (Protarga) | CA-4 (OXiGENE) |
| Aromatase inhibitors | Aminoglutethimide | Exemestan |
| | Letrozole | Atamestan (BioMedicines) |
| | Anastrazole | YM-511 (Yamanouchi) |
| | Formestan | |
| Thymidylate synthase inhibitors | Pemetrexed (Eli Lilly) | Nolatrexed (Eximias) |
| | ZD-9331 (BTG) | CoFactor ™ (BioKeys) |
| DNA antagonists | Trabectedin (PharmaMar) | Mafosfamide (Baxter International) |
| | Glufosamide (Baxter International) | Apaziquone (Spectrum Pharmaceuticals) |
| | Albumin + 32P (Isotope Solutions) | O6-Benzylguanine (Paligent) |
| | Thymectacin (NewBiotics) | |
| | Edotreotid (Novartis) | |

TABLE 1-continued

| Category | Drugs | |
|---|---|---|
| Farnesyl transferase inhibitors | Arglabin (NuOncology Labs) | Tipifarnib (Johnson & Johnson) |
| | Ionafarnib (Schering-Plough) | Perillyl alcohol (DOR BioPharma) |
| | BAY-43-9006 (Bayer) | |
| Pump inhibitors | CBT-1 (CBA Pharma) | Zosuquidar trihydrochloride (Eli Lilly) |
| | Tariquidar (Xenova) | |
| | MS-209 (Schering AG) | Biricodar dicitrate (Vertex) |
| Histone acetyl transferase inhibitors | Tacedinaline (Pfizer) | Pivaloyloxymethyl butyrate (Titan) |
| | SAHA (Aton Pharma) | |
| | MS-275 (Schering AG) | Depsipeptide (Fujisawa) |
| Metalloproteinase inhibitors | Neovastat (Aeterna Laboratories) | CMT-3 (CollaGenex) |
| | Marimastat (British Biotech) | BMS-275291 (Celltech) |
| Ribonucleoside reductase inhibitors | Gallium maltolate (Titan) | Tezacitabine (Aventis) |
| | Triapin (Vion) | Didox (Molecules for Health) |
| TNF-alpha agonists/ antagonists | Virulizin (Lorus Therapeutics) | Revimid (Celgene) |
| | CDC-394 (Celgene) | |
| Endothelin-A receptor antagonists | Atrasentan (Abbot) | YM-598 (Yamanouchi) |
| | ZD-4054 (AstraZeneca) | |
| Retinoic acid receptor agonists | Fenretinide (Johnson & Johnson) | Alitretinoin (Ligand) |
| | LGD-1550 (Ligand) | |
| Immunomodulators | Interferon | Dexosome therapy (Anosys) |
| | Oncophage (Antigenics) | Pentrix (Australian Cancer Technology) |
| | GMK (Progenics) | |
| | Adenocarcinoma vaccine (Biomira) | JSF-154 (Tragen) |
| | | Cancer vaccine (Intercell) |
| | CTP-37 (AVI BioPharma) | Norelin (Biostar) |
| | JRX-2 (Immuno-Rx) | BLP-25 (Biomira) |
| | PEP-005 (Peplin Biotech) | MGV (Progenics) |
| | Synchrovax vaccines (CTL Immuno) | !3-Alethin (Dovetail) |
| | | CLL-Thera (Vasogen) |
| | Melanoma vaccine (CTL Immuno) | |
| | p21-RAS vaccine (GemVax) | |
| Hormonal and antihormonal agents | Oestrogens | Prednisone |
| | Conjugated oestrogens | Methylprednisolone |
| | Ethynyloestradiol | Prednisolone |
| | chlorotrianisene | Aminoglutethimide |
| | Idenestrol | Leuprolide |
| | Hydroxyprogesterone caproate | Goserelin |
| | | Leuporelin |
| | Medroxyprogesterone | Bicalutamide |
| | Testosterone | Flutamide |
| | Testosterone propionate | Octreotide |
| | Fluoxymesterone | Nilutamide |
| | Methyltestosterone | Mitotan |
| | Diethylstilbestrol | P-04 (Novogen) |
| | Megestrol | 2-methoxyoestradiol (EntreMed) |
| | Tamoxifen | |
| | Toremofin | Arzoxifen (Eli Lilly) |
| | Dexamethasone | |
| Photodynamic agents | Talaporfin (Light Sciences) | Pd-Bacteriopheophorbid (Yeda) |
| | Theralux (Theratechnologies) | |
| | Motexafin-Gadolinium (Pharmacyclics) | Lutetium-Texaphyrin (Pharmacyclics) |
| | | Hypericin |
| Tyrosine kinase inhibitors | Imatinib (Novartis) | Kahalide F (PharmaMar) |
| | Leflunomide (Sugen/Pharmacia) | CEP-701 (Cephalon) |
| | ZDI839 (AstraZeneca) | CEP-751 (Cephalon) |
| | Erlotinib (Oncogene Science) | MLN518 (Millenium) |
| | Canertjnib (Pfizer) | PKC412 (Novartis) |
| | Squalamine (Genaera) | Phenoxodiol O |
| | SU5416 (Pharmacia) | Trastuzumab (Genentech) |
| | SU6668 (Pharmacia) | C225 (ImClone) |
| | ZD4190 (AstraZeneca) | rhu-Mab (Genentech) |
| | ZD6474 (AstraZeneca) | MDX-H210 (Medarex) |
| | Vatalanib (Novartis) | 2C4 (Genentech) |
| | PKI166 (Novartis) | MDX-447 (Medarex) |
| | GW2016 (GlaxoSmithKline) | ABX-EGF (Abgenix) |
| | | IMC-1C11 (ImClone) |
| | EKB-509 (Wyeth) | |
| | EKB-569 (Wyeth) | |

TABLE 1-continued

| | | |
|---|---|---|
| Various agents | SR-27897 (CCK-A inhibitor, Sanofi-Synthelabo) | BCX-1777 (PNP inhibitor, BioCryst) |
| | Tocladesine (cyclic AMP agonist, Ribapharm) | Ranpirnase (ribonuclease stimulant, Alfacell) |
| | Alvocidib (CDK inhibitor, Aventis) | Galarubicin (RNA synthesis inhibitor, Dong-A) |
| | CV-247 (COX-2 inhibitor, Ivy Medical) | Tirapazamine (reducing agent, SRI International) |
| | P54 (COX-2 inhibitor, Phytopharm) | N-Acetylcysteine (reducing agent, Zambon) |
| | CapCell ™ (CYP450 stimulant, Bavarian Nordic) | R-Flurbiprofen (NF-kappaB inhibitor, Encore) |
| | GCS-IOO (gal3 antagonist, GlycoGenesys) | 3CPA (NF-kappaB inhibitor, Active Biotech) |
| | G17DT immunogen (gastrin inhibitor, Aphton) | Seocalcitol (vitamin D receptor agonist, Leo) |
| | Efaproxiral (oxygenator, Allos Therapeutics) | 131-I-TM-601 (DNA antagonist, TransMolecular) |
| | PI-88 (heparanase inhibitor, Progen) | Eflornithin (ODC inhibitor, ILEX Oncology) |
| | Tesmilifen (histamine antagonist, YM BioSciences) | Minodronic acid (osteoclast inhibitor, Yamanouchi) |
| | Histamine (histamine H2 receptor agonist, Maxim) | Indisulam (p53 stimulant, Eisai) |
| | Tiazofurin (IMPDH inhibitor, Ribapharm) | Aplidin (PPT inhibitor, PharmaMar) |
| | Cilengitide (integrin antagonist, Merck KGaA) | Rituximab (CD20 antibody, Genentech) |
| | SR-31747 (IL-1 antagonist, Sanofi-Synthelabo) | Gemtuzumab (CD33 antibody, Wyeth Ayerst) |
| | CCI-779 (mTOR kinase inhibitor, Wyeth) | PG2 (haematopoiesis promoter, Pharmagenesis) |
| | Exisulind (PDE-V inhibitor, Cell Pathways) | Immunol ™ (triclosan mouthwash, Endo) |
| | CP-461 (PDE-V inhibitor, Cell Pathways) | Triacetyluridine (uridine prodrug, Wellstat) |
| | AG-2037 (GART inhibitor, Pfizer) | SN-4071 (sarcoma agent, Signature BioScience) |
| | WX-UK1 (plasminogen activator inhibitor, Wilex) | TransMID-107 ™ (immunotoxin, KS Biomedix) |
| | PBI-1402 (PMN stimulant, ProMetic LifeSciences) | PCK-3145 (apoptosis promoter, Procyon) |
| | Bortezomib (proteasome inhibitor, Millennium) | Doranidazole (apoptosis promoter, Pola) |
| | SRL-172 (T-cell stimulant, SR Pharma) | CHS-828 (cytotoxic agent, Leo) |
| | TLK-286 (glutathione-S transferase inhibitor, Telik) | Trans-retinic acid (differentiator, NIH) |
| | PT-100 (growth factor agonist, Point Therapeutics) | MX6 (apoptosis promoter, MAXIA) |
| | Midostaurin (PKC inhibitor, Novartis) | Apomine (apoptosis promoter, ILEX Oncology) |
| | Bryostatin-1 (PKC stimulant, GPC Biotech) | Urocidin (apoptosis promoter, Bioniche) |
| | CDA-II (apoptosis promoter, Everlife) | Ro-31-7453 (apoptosis promoter, La Roche) |
| | SDX-101 (apoptosis promoter, Salmedix) | Brostallicin (apoptosis promoter, Pharmacia) |
| | Ceflatonin (apoptosis promoter, ChemGenex) | |
| Alkylating agents | Cyclophosphamide | Lomustine |
| | Busulfan | Procarbazine |
| | Ifosfamide | Altretamine |
| | Melphalan | Estramustine phosphate |
| | Hexamethylmelamine | Mechloroethamine |
| | Thiotepa | Streptozocin |
| | chloroambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (Aeterna) |
| | Carboxyphthalatoplatinum | Satraplatin (Johnson Matthey) |
| | Tetraplatin | BBR-3464 (Hoffmann-La Roche) |
| | Ormiplatin | SM-11355 (Sumitomo) |
| | Iproplatin | AP-5280 (Access) |

TABLE 1-continued

| | | |
|---|---|---|
| Antimetabolites | Azacytidine | Tomudex |
| | Gemcitabine | Trimetrexate |
| | Capecitabine | Deoxycoformycin |
| | 5-fluoroouracil | Fludarabine |
| | Floxuridine | Pentostatin |
| | 2-chlorodesoxyadenosine | Raltitrexed |
| | 6-Mercaptopurine | Hydroxyurea |
| | 6-Thioguanine | Decitabine (SuperGen) |
| | Cytarabine | Clofarabine (Bioenvision) |
| | 2-fluoroodesoxycytidine | Irofulven (MGI Pharma) |
| | Methotrexate | DMDC (Hoffmann-La Roche) |
| | Idatrexate | Ethynylcytidine (Taiho) |
| Topoisomerase inhibitors | Amsacrine | Rubitecan (SuperGen) |
| | Epirubicin | Exatecan mesylate (Daiichi) |
| | Etoposide | |
| | Teniposide or mitoxantrone | Quinamed (ChemGenex) |
| | | Gimatecan (Sigma-Tau) |
| | Irinotecan (CPT-11) | Diflomotecan (Beaufour-Ipsen) |
| | 7-Ethyl-10-hydroxycamptothecin | TAS-103 (Taiho) |
| | Topotecan | Elsamitrucin (Spectrum) |
| | Dexrazoxanet (TopoTarget) | J-107088 (Merck & Co) |
| | | BNP-1350 (BioNumerik) |
| | Pixantrone (Novuspharrna) | CKD-602 (Chong Kun Dang) |
| | Rebeccamycin analogue (Exelixis) | KW-2170 (Kyowa Hakko) |
| | BBR-3576 (Novuspharrna) | |
| Antitumour antibiotics | Dactinomycin (Actinomycin D) | Amonafide |
| | | Azonafide |
| | Doxorubicin (Adriamycin) | Anthrapyrazole |
| | Deoxyrubicin | Oxantrazole |
| | Valrubicin | Losoxantrone |
| | Daunorubicin (Daunomycin) | Bleomycin sulfate (Blenoxan) |
| | Epirubicin | Bleomycinic acid |
| | Therarubicin | Bleomycin A |
| | Idarubicin | Bleomycin B |
| | Rubidazon | Mitomycin C |
| | Plicamycinp | MEN-10755 (Menarini) |
| | Porfiromycin | GPX-100 (Gem Pharmaceuticals) |
| | Cyanoomorpholinodoxo-rubicin | |
| | Mitoxantron (Novantron) | |
| Antimitotic agents | Paclitaxel | SB 408075 (GlaxoSmithKline) |
| | Docetaxel | |
| | Colchicine | E7010 (Abbott) |
| | Vinblastine | PG-TXL (Cell Therapeutics) |
| | Vincristine | |
| | Vinorelbine | IDN 5109 (Bayer) |
| | Vindesine | A 105972 (Abbott) |
| | Dolastatin 10 (NCI) | A 204197 (Abbott) |
| | Rhizoxin (Fujisawa) | LU 223651 (BASF) |
| | Mivobulin (Warner-Lambert) | D 24851 (ASTA Medica) |
| | | ER-86526 (Eisai) |
| | Cemadotin (BASF) | Combretastatin A4 (BMS) |
| | RPR 109881A (Aventis) | Isohomohalichondrin-B (PharmaMar) |
| | TXD 258 (Aventis) | |
| | Epothilone B (Novartis) | ZD 6126 (AstraZeneca) |
| | T 900607 (Tularik) | PEG-Paclitaxel (Enzon) |
| | T 138067 (Tularik) | AZ10992 (Asahi) |
| | Cryptophycin 52 (Eli Lilly) | !DN-5109 (Indena) |
| | Vinflunine (Fabre) | AVLB (Prescient NeuroPharma) |
| | Auristatin PE (Teikoku Hormone) | Azaepothilon B (BMS) |
| | BMS 247550 (BMS) | BNP-7787 (BioNumerik) |
| | BMS 184476 (BMS) | CA-4-Prodrug (OXiGENE) |
| | BMS 188797 (BMS) | Dolastatin-10 (NrH) |
| | Taxoprexin (Protarga) | CA-4 (OXiGENE) |
| Aromatase inhibitors | Aminoglutethimide | Exemestan |
| | Letrozole | Atamestan (BioMedicines) |
| | Anastrazole | YM-511 (Yamanouchi) |
| | Formestan | |
| Thymidylate synthase inhibitors | Pemetrexed (Eli Lilly) | Nolatrexed (Eximias) |
| | ZD-9331 (BTG) | CoFactor™ (BioKeys) |
| DNA antagonists | Trabectedin (PharmaMar) | Mafosfamide (Baxter International) |
| | Glufosfamide (Baxter International) | Apaziquone (Spectrum |

TABLE 1-continued

| Category | | |
|---|---|---|
| | Albumin + 32P (Isotope Solutions) | Pharmaceuticals) |
| | Thymectacin (NewBiotics) | O6-benzylguanine (Paligent) |
| | Edotreotid (Novartis) | |
| Farnesyl transferase inhibitors | Arglabin (NuOncology Labs) | Tipifarnib (Johnson & Johnson) |
| | Ionafarnib (Schering-Plough) | Perillyl alcohol (DOR BioPharma) |
| | BAY-43-9006 (Bayer) | |
| Pump inhibitors | CBT-1 (CBA Pharma) | Zosuquidar trihydrochloride (Eli Lilly) |
| | Tariquidar (Xenova) | |
| | MS-209 (Schering AG) | Biricodar dicitrate (Vertex) |
| Histone acetyl transferase inhibitors | Tacedinaline (Pfizer) | Pivaloyloxymethyl butyrate (Titan) |
| | SAHA (Aton Pharma) | |
| | MS-275 (Schering AG) | Depsipeptide (Fujisawa) |
| Metalloproteinase inhibitors | Neovastat (Aeterna Laboratories) | CMT-3 (CollaGenex) |
| | | BMS-275291 (Celltech) |
| Ribonucleoside reductase inhibitors | Marimastat (British Biotech) | Tezacitabine (Aventis) |
| | Gallium maltolate (Titan) | Didox (Molecules for Health) |
| | Triapin (Vion) | |
| TNF-alpha agonists/ antagonists | Virulizin (Lorus Therapeutics) | Revimid (Celgene) |
| | CDC-394 (Celgene) | |
| Endothelin-A receptor antagonists | Atrasentan (Abbot) | YM-598 (Yamanouchi) |
| | ZD-4054 (AstraZeneca) | |
| Retinoic acid receptor agonists | Fenretinide (Johnson & Johnson) | Alitretinoin (Ligand) |
| | LGD-1550 (Ligand) | |
| Immuno-modulators | Interferon | Dexosome therapy (Anosys) |
| | Oncophage (Antigenics) | |
| | GMK (Progenics) | Pentrix (Australian Cancer Technology) |
| | Adenocarcinoma vaccine (Biomira) | |
| | | JSF-154 (Tragen) |
| | CTP-37 (AVI BioPharma) | Cancer vaccine (Intercell) |
| | JRX-2 (Immuno-Rx) | Norelin (Biostar) |
| | PEP-005 (Peplin Biotech) | BLP-25 (Biomira) |
| | Synchrovax vaccines (CTL Immuno) | MGV (Progenics) |
| | | !3-Alethin (Dovetail) |
| | Melanoma vaccine (CTL Immuno) | CLL-Thera (Vasogen) |
| | p21-RAS vaccine (GemVax) | |
| Hormonal and antihormonal agents | Oestrogens | Prednisone |
| | Conjugated oestrogens | Methylprednisolone |
| | Ethynyloestradiol | Prednisolone |
| | chlorotrianisene | Aminoglutethimide |
| | Idenestrol | Leuprolide |
| | Hydroxyprogesterone caproate | Goserelin |
| | | Leuporelin |
| | Medroxyprogesterone | Bicalutamide |
| | Testosterone | Flutamide |
| | Testosterone propionate | Octreotide |
| | Fluoxymesterone | Nilutamide |
| | Methyltestosterone | Mitotan |
| | Diethylstilbestrol | P-04 (Novogen) |
| | Megestrol | 2-methoxyoestradiol (EntreMed) |
| | Tamoxifen | |
| | Toremofin | Arzoxifen (Eli Lilly) |
| | Dexamethasone | |
| Photodynamic agents | Talaporfin (Light Sciences) | Pd-Bacteriopheophorbid (Yeda) |
| | Theralux (Theratechnologies) | Lutetium-Texaphyrin (Pharmacyclics) |
| | Motexafin-Gadolinium (Pharmacyclics) | Hypericin |
| Tyrosine kinase inhibitors | Imatinib (Novartis) | Kahalide F (PharmaMar) |
| | Leflunomide(Sugen/Pharmacia) | CEP-701 (Cephalon) |
| | ZDI839 (AstraZeneca) | CEP-751 (Cephalon) |
| | Erlotinib (Oncogene Science) | MLN518 (Millenium) |
| | | PKC412 (Novartis) |
| | Canertjnib (Pfizer) | Phenoxodiol O |
| | Squalamine (Genaera) | Trastuzumab (Genentech) |
| | SU5416 (Pharmacia) | C225 (ImClone) |
| | SU6668 (Pharmacia) | rhu-Mab (Genentech) |
| | ZD4190 (AstraZeneca) | MDX-H210 (Medarex) |
| | ZD6474 (AstraZeneca) | 2C4 (Genentech) |
| | Vatalanib (Novartis) | MDX-447 (Medarex) |
| | PKI166 (Novartis) | ABX-EGF (Abgenix) |

TABLE 1-continued

| | | |
|---|---|---|
| | GW2016 (GlaxoSmith-Kline) EKB-509 (Wyeth) EKB-569 (Wyeth) | IMC-1C11 (ImClone) |
| Various agents | SR-27897 (CCK-A inhibitor, Sanofi-Synthelabo) Tocladesine (cyclic AMP agonist, Ribapharm) Alvocidib (CDK inhibitor, Aventis) CV-247 (COX-2 inhibitor, Ivy Medical) P54 (COX-2 inhibitor, Phytopharm) CapCell ™ (CYP450 stimulant, Bavarian Nordic) GCS-IOO (gal3 antagonist, GlycoGenesys) G17DT immunogen (gastrin inhibitor, Aphton) Efaproxiral (oxygenator, Allos Therapeutics) PI-88 (heparanase inhibitor, Progen) Tesmilifen (histamine antagonist, YM BioSciences) Histamine (histamine H2 receptor agonist, Maxim) Tiazofurin (IMPDH inhibitor, Ribapharm) Cilengitide (integrin antagonist, Merck KGaA) SR-31747 (IL-1 antagonist, Sanofi-Synthelabo) CCI-779 (mTOR kinase inhibitor, Wyeth) Exisulind (PDE-V inhibitor, Cell Pathways) CP-461 (PDE-V inhibitor, Cell Pathways) AG-2037 (GART inhibitor, Pfizer) WX-UK1 (plasminogen activator inhibitor, Wilex) PBI-1402 (PMN stimulant, ProMetic LifeSciences) Bortezomib (proteasome inhibitor, Millennium) SRL-172 (T-cell stimulant, SR Pharma) TLK-286 (glutathione-S transferase inhibitor, Telik) PT-100 (growth factor agonist, Point Therapeutics) Midostaurin (PKC inhibitor, Novartis) Bryostatin-1 (PKC stimulant, GPC Biotech) CDA-II (apoptosis promoter, Everlife) SDX-101 (apoptosis promoter, Salmedix) Ceflatonin (apoptosis promoter, ChemGenex) | BCX-1777 (PNP inhibitor, BioCryst) Ranpirnase (ribonuclease stimulant, Alfacell) Galarubicin (RNA synthesis inhibitor, Dong-A) Tirapazamine (reducing agent, SRI International) N-Acetylcysteine (reducing agent, Zambon) R-Flurbiprofen (NF-kappaB inhibitor, Encore) 3CPA (NF-kappaB inhibitor, Active Biotech) Seocalcitol (vitamin D receptor agonist, Leo) 131-I-TM-601 (DNA antagonist, TransMolecular) Eflornithin (ODC inhibitor, ILEX Oncology) Minodronic acid (osteoclast inhibitor, Yamanouchi) Indisulam (p53 stimulant, Eisai) Aplidin (PPT inhibitor, PharmaMar) Rituximab (CD20 antibody, Genentech) Gemtuzumab (CD33 antibody, Wyeth Ayerst) PG2 (haematopoiesis promoter, Pharmagenesis) Immunol ™ (triclosan mouthwash, Endo) Triacetyluridine (uridine prodrug, Wellstat) SN-4071 (sarcoma agent, Signature BioScience) TransMID-107 ™ (immunotoxin, KS Biomedix) PCK-3145 (apoptosis promoter, Procyon) Doranidazole (apoptosis promoter, Pola) CHS-828 (cytotoxic agent, Leo) Trans-retinic acid (differentiator, NIH) MX6 (apoptosis promoter, MAXIA) Apomine (apoptosis promoter, ILEX Oncology) Urocidin (apoptosis promoter, Bioniche) Ro-31-7453 (apoptosis promoter, La Roche) Brostallicin (apoptosis promoter, Pharmacia) |

A combined treatment of this type can be achieved with the aid of simultaneous, consecutive or separate dispensing of the individual components of the treatment. Combination products of this type employ the compounds according to the invention.

2. The present compounds according to the invention are suitable as pharmaceutical active ingredients for mammals, in particular for humans, in the treatment of SGK-induced diseases.

The invention thus relates to the use of compounds according to claim 1, and pharmaceutically usable derivatives, solvates and stereoisomers thereof, including mixtures thereof in all ratios, for the preparation of a medicament for the treatment of diseases in which the inhibition, regulation and/or modulation of kinase signal transduction plays a role.

Preference is given to the use of compounds according to claim 1, and pharmaceutically usable derivatives, solvates and stereoisomers thereof, including mixtures thereof in all ratios, for the preparation of a medicament for the treatment of diseases which are influenced by inhibition of SGKs by the compounds according to claim 1.

The present invention encompasses the use of the compounds according to claim 1 according to the invention and/or physiologically acceptable salts and solvates thereof for the preparation of a medicament for the treatment or prevention of diabetes (for example diabetes mellitus, diabetic nephropathy, diabetic neuropathy, diabetic angiopathy and microangiopathy), obesity, metabolic syndrome (dyslipidaemia), systemic and pulmonary hypertonia, cardiovascular diseases (for example cardiac fibroses after myocardial infarction, cardiac hypertrophy and cardiac insufficiency, arteriosclerosis) and renal diseases (for example glomerulosclerosis, nephrosclerosis, nephritis, nephropathy, electrolyte excretion disorder), generally in fibroses and inflammatory processes of any type (for example liver cirrhosis, pulmonary fibrosis, fibrosing pancreatitis, rheumatism and arthroses, Crohn's disease, chronic bronchitis, radiation fibrosis, sclerodermatitis, cystic fibrosis, scarring, Alzheimer's disease).

The compounds according to the invention can also inhibit the growth of cancer, tumour cells and tumour metastases and are therefore suitable for tumour therapy.

The compounds according to the invention are furthermore used for the treatment of coagulopathies, such as, for example, dysfibrinogenaemia, hypoproconvertinaemia, haemophilia B, Stuart-Prower defect, prothrombin complex deficiency, consumption coagulopathy, hyperfibrinolysis, immuno-coagulopathy or complex coagulopathies, and also in neuronal excitability, for example epilepsy. The compounds according to the invention can also be employed therapeutically in the treatment of glaucoma or a cataract. The compounds according to the invention are furthermore used in the treatment of bacterial infections and in antiinfection therapy. The compounds according to the invention can also be employed therapeutically for increasing learning ability and attention.

Preference is given to the use of compounds according to claim 1, and pharmaceutically usable derivatives, solvates and stereoisomers thereof, including mixtures thereof in all ratios, for the preparation of a medicament for the treatment or prevention of diabetes, obesity, metabolic syndrome (dyslipidaemia), systemic and pulmonary hypertonia, cardiovascular diseases and renal diseases, generally in fibroses and inflammatory processes of any type, cancer, tumour cells, tumour metastases, coagulopathies, neuronal excitability, glaucoma, cataract, bacterial infections and in anti-infection therapy, for increasing learning ability and attention, and for the treatment and prophylaxis of cell ageing and stress.

Diabetes is preferably diabetes mellitus, diabetic nephropathy, diabetic neuropathy, diabetic angiopathy and microangiopathy.

Cardiovascular diseases are preferably cardiac fibroses after myocardial infarction, cardiac hypertrophy, cardiac insufficiency and arteriosclerosis.

Renal diseases are preferably glomerulosclerosis, nephrosclerosis, nephritis, nephropathy and electrolyte excretion disorder.

Fibroses and inflammatory processes are preferably liver cirrhosis, pulmonary fibrosis, fibrosing pancreatitis, rheumatism and arthroses, Crohn's disease, chronic bronchitis, radiation fibrosis, sclerodermatitis, cystic fibrosis, scarring, Alzheimer's disease.

Assays

The compounds according to the invention described in the examples can be tested for a kinase-inhibiting action by the assays described below. Other assays are known from the literature and can readily be performed by the person skilled in the art (see, for example, Dhanabal et al., *Cancer Res.* 59:189-197; Xin et al., *J. Biol. Chem.* 274:9116-9121; Sheu et al., *Anticancer Res.* 18:4435-4441; Ausprunk et al., *Dev. Biol.* 38:237-248; Gimbrone et al., *J. Natl. Cancer Inst.* 52:413-427; Nicosia et al., *In Vitro* 18:538-549).

Measurement of the CHK1 Kinase Activity

CHK1 kinase is expressed for the purposes of protein production in insect cells (Sf21; *S. frugiperda*) and subsequent purification by affinity chromatography as fusion protein with glutathione S-transferase in a baculovirus expression vector. The cultivation, infection and digestion of the cells as well as the purification of the fusion protein by column chromatography are carried out in accordance with manufacturer-oriented generic working instructions.

The kinase activity is measured using various available measurement systems. In the scintillation proximity method (Sorg et al., J. of. Biomolecular Screening, 2002, 7, 11-19), the flashplate method or the filter binding test, the radioactive phosphorylation of a protein or peptide as substrate is measured using radioactively labelled ATP ($^{32}$P-ATP, $^{33}$P-ATP). In the case of the presence of an inhibitory compound, a reduced radioactive signal, or none at all, can be detected. Furthermore, homogeneous time-resolved fluorescence resonance energy transfer (HTR-FRET) and fluorescence polarisation (FP) technologies are useful as assay methods (Sills et al., J. of Biomolecular Screening, 2002, 191-214).

Other non-radioactive ELISA assay methods use specific phospho antibodies (phospho ABs). The phospho antibody only binds the phosphorylated substrate. This binding can be detected by chemiluminescence using a second peroxidase-conjugated antibody (Ross et al., 2002, Biochem. J.).

Flashplate Method (CHK1):

The test plates used are 384-well streptavidin-coated Flashplates Plus®from Perkin Elmer (Cat. No. SMP410A001 PK). The assay plate is equilibrated with 75 µl of assay buffer per well 30 min before commencement of the experiment. The buffer is sucked out before commencement of the experiment, and the components of the kinase reaction described below are pipetted onto the plate.

CHK1 kinase, a biotinylated substrate peptide (for example CHKtide: KKKVSRSGLYRSPSMPENLNRPR), is incubated with radioactively labelled ATP in the presence and absence of test substances at 30° Celsius and a total volume of 50 µl. The reaction is terminated using 25 µl of a 0.2 M EDTA solution. After incubation for 30 min at room temperature, the supernatants are filtered off with suction, and the wells are washed three times with 100 µl of 0.9% NaCl solution each time. The measurement of the bound radioactivity is carried out by means of a scintillation measuring instrument (Topcount NXT, Perkin-Elmer).

The full value used is the inhibitor-free kinase reaction. This should be approximately in the range 3000-4000 cpm. The pharmacological zero value used is staurosporin in a final concentration of 0.1 µM. The inhibitory values (IC50) are determined using the program RS1_MTS ( ).

Kinase reaction conditions per well:

5-20 mU of CHK1 kinase 0.15 µg of CHKtide (KKKVSRSGLYRSPSMPENLNRPR)

8 µM of ATP, cold 0.2 µCi of $^{33}$P-ATP

50 µl total volume (1-fold assay buffer reaction conditions)
  Solutions used:
    assay buffer:

50 mM Tris 0.1 mM Titriplex VI (EGTA 10 mM magnesium acetate 0.1% mercaptoethanol 0.02% Brij35 pH=7.5 (to be set using hydrochloric acid)

Bovine serum albumin (final concentration 0.1%) is not added until just before use.
  stop solution:

0.2 M TitriplexIII (EDTA)
  $^{33}$P-ATP (Perkin-Elmer)
  CHK1 kinase preparations: specific activity>50 U/mg
  CHKtide solution: biotinylated peptide substrate (Biotrend) stored as stock solution (concentration 0.15 mg/ml).

Filter Binding Method (CHK1):

5-20 mU of CHK1 kinase (diluted in 20 mM MOPS pH7.5, 1 mM EDTA, 0.1% β-mercaptoethanol, 0.01% Brij-35, 5% glycerol, 1 mg/ml of BSA) are incubated for 30 min at room temperature in the presence of 30-200 µM CHKtide in 25.5 µl in 1-fold reaction buffer (8 mM MOPS pH7, 0.2 mM EDTA, 10 mM magnesium acetate, 0.02 mM $^{33}$P-ATP [500-1000 cpm/pmol]). The reaction is stopped using 5 µl of 0.5 M ortho-phosphoric acid and filtered through P81 filter plates. After the filter plates have been washed a number of times, the bound radioactivity is determined in a scintillation counter.

Measurement of the CHK2 Kinase Activity

Filter Binding Method (CHK2):

5-20 mU of CHK2 kinase (diluted in 20 mM MOPS pH7.5, 1 mM EDTA, 0.1% β-mercaptoethanol, 0.01% Brij-35, 5% glycerol, 1 mg/ml of BSA) are incubated for 30 min at room temperature in the presence of 30-200 µM CHKtide (KKKVSRSGLYRSPSMPENLNRPR) in 25.5 µl in 1-fold reaction buffer (8 mM MOPS pH7, 0.2 mM EDTA, 10 mM magnesium acetate, 0.02 mM $^{33}$P-ATP [500-1000 cpm/pmol]). The reaction is stopped using 5 µl of 0.5 M ortho-phosphoric acid and filtered through P81 filter plates. After the filter plates have been washed a number of times, the bound radioactivity is determined in a scintillation counter.

The inhibition of SGK1 protein kinase can be determined in the filter binding method (analogously to CHK1, CHK2).

Above and below, all temperatures are indicated in ° C. In the following examples, "conventional work-up" means: if necessary, water is added, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation. Rf values on silica gel; eluent: ethyl acetate/methanol 9:1.

Mass spectrometry (MS):
  EI (electron impact ionisation) M$^+$
  FAB (fast atom bombardment) (M+H)$^+$
  ESI (electrospray ionisation) (M+H)$^+$ (unless indicated otherwise)
  APCI-MS (atmospheric pressure chemical ionisation—mass spectrometry) (M+H)$^+$.

HPLC Method A:

Column: Chromolith Speed ROD

RP-18e 50-4.6 mm

Eluent:

A: water+0.1% of TFA

B: acetonitrile+0.1% of TFA

Gradient:

0.0 min 4% of B 2.6 min 100% of B 3.3 min 100% of B wavelength: 220 nm

HPLC Method B:

Hewlett Packard HP 1100 series system with the following features: ion source: electrospray (positive mode); scan: 100-1000 m/e; fragmentation voltage: 60 V; gas temperature: 300° C., DAD: 220 nm.

Flow rate: 2.4 ml/min. The splitter used reduces the flow rate for the MS to 0.75 ml/min after the DAD.

Column:

Chromolith Speed ROD

RP-18e 50-4.6 mm

Solvent: LiChrosolv grade from Merck KGaA

Solvent A: H$_2$O (0.01% of TFA)

Solvent B: acetonitrile (0.008% of TFA)

Gradient:

20% of B→100% of B: 0 min. to 2.8 min.

100% of B: 2.8 min. to 3.3 min.

100% of B→20% B: 3.3 min. to 4 min.

Gradient for "polar" condition:

5% of B→100% of B: 0 min. to 3 min.

100% of B: 3 min. to 3.5 min.

100% of B 5% of B: 3.5 min. to 3.6 min.

EXAMPLE 1

1.1 5-(3-Cyano-4-fluorophenyl)furan-2-carboxylic acid 5.2 g of 4-fluoro-3-cyanobenzeneboronic acid, 6.5 g of 5-bromofuran-2-carboxylic acid, 5.6 g of sodium hydrogencarbonate, 0.5 g of tetrakis-(triphenylphosphine)palladium (0), 40 ml of toluene, 32 ml of THF and 40 ml of water are degassed a number of times and blanketed with nitrogen. The reaction mixture is stirred vigorously at a bath temperature of 90° C. under nitrogen for 3 hours. After cooling, the mixture is poured into water and extracted three times with ethyl acetate (EA). The aqueous phase is acidified at 0° C. using conc. hydrochloric acid and extracted a number of times with EA. This organic phase is washed with water, dried and evaporated to dryness, giving 4.2 g of a beige powder having a product content of 75% (according to HPLC-MS).

1.2 5-(3-Amino-1H-indazol-5-yl)furan-2-carboxylic acid 4.2 g of 5-(3-cyano-4-fluorophenyl)furan-2-carboxylic acid and 4.5 g of hydrazium hydroxide are heated overnight at 90° C. in 80 ml of butanol. The reaction mixture is subsequently evaporated, taken up in 1 N NaOH and extracted a number of times with EA. The aqueous phase is acidified using hydrochloric acid, and the precipitated solid is filtered off with suction. This is triturated with MTBE, filtered off with suction again and dried, giving 4.0 g of 5-(3-amino-1H-indazol-5-yl)furan-2-carboxylic acid as brownish solid (91%).

1.3 Ethyl 5-(3-amino-1H-indazol-5-yl)furan-2-carboxylate ("A2")

100 mg of 5-(3-amino-1H-indazol-5-yl)furan-2-carboxylic acid and 78 mg of p-toluenesulfonic acid are heated at 75° C. for 3 days in 5 ml of ethanol. The batch is evaporated, water is added, and the mixture is neutralised. The mixture is extracted three times with EA, the combined org. phases are washed with water, dried and evaporated to dryness. Purification by RP chromatography gives 30 mg of ethyl 5-(3-amino-1H-indazol-5-yl)furan-2-carboxylate, corresponding to a yield of 27%.

An analogous procedure using methanol for the esterification gives the compound methyl 5-(3-amino-1H-indazol-5-yl)furan-2-carboxylate ("A1").

EXAMPLE 2

2.1 tert-Butyl 5-(3-cyano-4-fluorophenyl)furan-2-carboxylate 12.9 g of 4-fluoro-3-cyanobenzeneboronic acid, 14.8 g of tert-butyl 5-bromofuran-2-carboxylate, 30.0 g of sodium hydrogencarbonate, 2.0 g of tetrakis(triphenylphosphine)palladium(0), 300 ml of ethylene glycol dimethyl ether and 200 ml of water are degassed a number of times and blanketed with nitrogen. The reaction mixture is stirred at a bath temperature of 90° C. under nitrogen for 24 hours. After cooling, the mixture is treated with water and ethyl acetate, and the phases are separated. The aqueous phase is extracted a number of times with ethyl acetate, the combined organic phases are dried and evaporated to dryness. The residue is treated firstly with PE, subsequently with a little EA and filtered off with suction (K1). The EA mother liquor is evaporated, and the residue is recrystallised from a little EA (K2) After drying, combination of K1 and K2 gives 11.8 g of tert-butyl 5-(3-cyano-4-fluorophenyl)furan-2-carboxylate (53%) as virtually colourless powder.

2.2 tert-Butyl 5-(3-amino-1H-indazol-5-yl)furan-2-carboxylate ("A2a")

3.74 g of tert-butyl 5-(3-cyano-4-fluorophenyl)furan-2-carboxylate and 4.5 g of hydrazium hydroxide are heated overnight at 90° C. in 10 ml of butanol. The reaction mixture is subsequently evaporated and purified by chromatography on a short silica gel column with EA, giving 2.9 g of tert-butyl 5-(3-amino-1H-indazol-5-yl)furan-2-carboxylate ("A2a") as colourless solid (74%).

An analogous procedure via isopropyl 5-(3-cyano-4-fluorophenyl)furan-2-carboxylate gives the compound isopropyl 5-(3-amino-1H-indazol-5-yl)-furan-2-carboxylate ("A7").

EXAMPLE 3

3.1 tert-Butyl 5-{3-[(5-chlorothiophene-2-carbonyl)amino]-1H-indazol-5-yl}furan-2-carboxylate 300 mg of tert-butyl 5-(3-amino-1H-indazol-5-yl)furan-2-carboxylate, 199 mg of 5-chlorothiophene-2-carbonyl chloride and 8 mg of 4-(dimethylamino)pyridine are stirred at 90° C. for 24 hours in 2 ml of pyridine and 100 µl of dioxane. The reaction mixture is evaporated, and the residue is purified by column chromatography. Yield: 260 mg (58%) of tert-butyl 5-{3-[(5-chlorothiophene-2-carbonyl)amino]-1H-indazol-5-yl}furan-2-carboxylate.

3.2 5-{3-[(5-Chlorothiophene-2-carbonyl)amino]-1H-indazol-5-yl}furan-2-carboxylic acid ("A20")

240 mg of tert-butyl 5-{3-[(5-chlorothiophene-2-carbonyl)amino]-1H-indazol-5-yl}furan-2-carboxylate are dissolved in 1 ml of trifluoroacetic acid and 3 ml of dichloromethane and stirred at room temperature for 24 hours. The batch is evaporated, the residue is stirred with dichloromethane, filtered off with suction and dried, giving 209 mg of 5-{3-[(5-chlorothiophene-2-carbonyl)amino]-1H-indazol-5-yl}furan-2-car-boxylic acid ("A20") (quant.).

The following compounds are obtained analogously

| No. | Chemical structure / Name | Retention time Rf [min] | HPLC method |
|---|---|---|---|
| "A3" | 5-(3-Acetylamino-1H-indazol-5-yl)furan-2-carboxylic acid | | |
| "A4" | 5-[3-(Cyclopropanecarbonylamino)-1H-indazol-5-yl]furan-2-carboxylic acid | 0.927 | A |
| "A5" | 5-(3-Benzoylamino-1H-indazol-5-yl)furan-2-carboxylic acid | | |
| "A6" | 5-[3-(4-Pentylbenzoylamino)-1H-indazol-5-yl]furan-2-carboxylic acid | 1.791 | A |

-continued

| No. | Chemical structure Name | Retention time Rf [min] | HPLC method |
|---|---|---|---|
| "A8" | 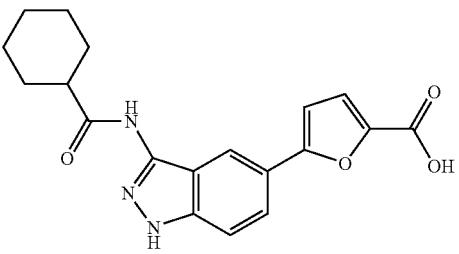<br>5-[3-(Cyclohexanecarbonylamino)-1H-indazol-5-yl]furan-2-carboxylic acid | 1.306 | A |
| "A9" | 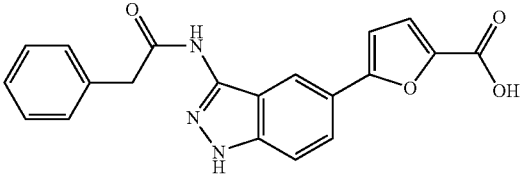<br>5-(3-Phenylacetylamino-1H-indazol-5-yl)-furan-2-carboxylic acid | 1.237 | A |
| "A10" | 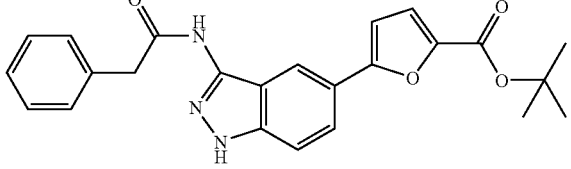<br>5-(3-Phenylacetylamino-1H-indazol-5-yl)-furan-2-carboxylic acid | 2.231 | A |
| "A11" | 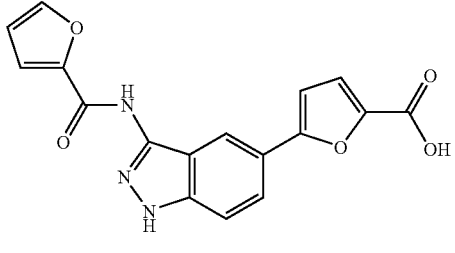<br>5-{3-[(Furan-2-carbonyl)amino]1H-indazol-5-yl}furan-2-carboxylic acid | 1.543 | A |
| "A12" | 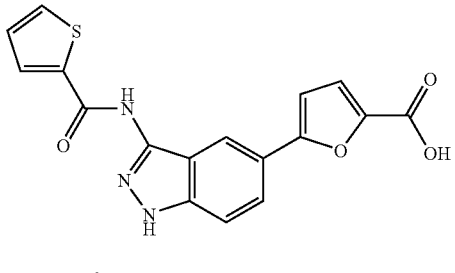<br>5-{3-[(Thiophene-2-carbonyl)amino]1H-indazol-5-yl}furan-2-carboxylic acid | 1.639 | A |

| | -continued | | |
|---|---|---|---|
| No. | Chemical structure<br>Name | Retention time<br>Rf [min] | HPLC<br>method |
| "A13" | 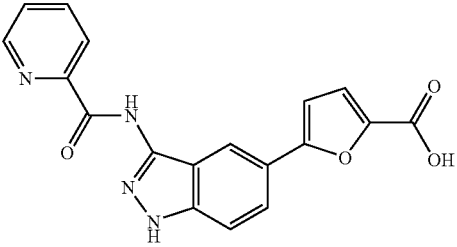<br>5-{3-[(Pyridine-2-carbonyl)amino]1H-indazol-<br>5-yl}furan-2-carboxylic acid | 1.653 | A |
| "A14" | 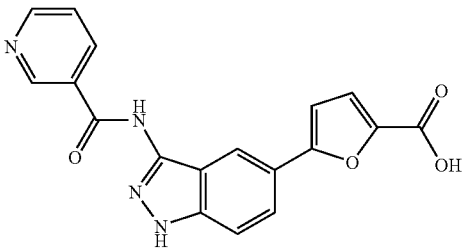<br>5-{3-[(Pyridine-3-carbonyl)amino]1H-indazol-<br>5-yl}furan-2-carboxylic acid | 1.333 | A |
| "A15" | 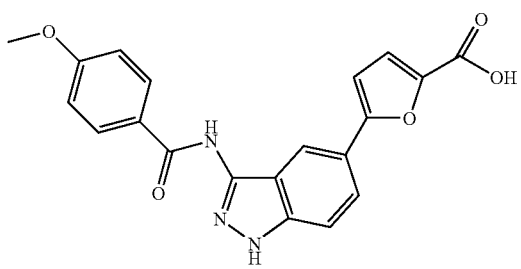<br>5-[3-(4-Methoxybenzoylamino)1H-indazol-5-<br>yl]furan-2-carboxylic acid | 1.712 | A |
| "A16" | 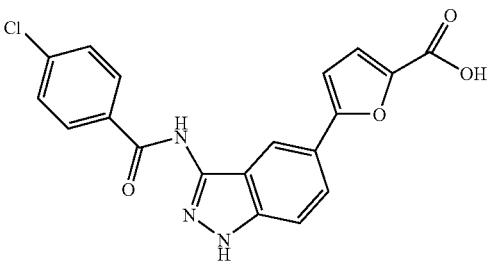<br>5-[3-(4-Chlorobenzoylamino)1H-indazol-5-yl]-<br>furan-2-carboxylic acid | 1.837 | A |

| No. | Chemical structure Name | Retention time Rf [min] | HPLC method |
|---|---|---|---|
| "A17" | 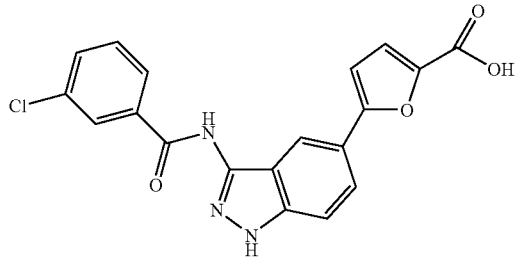<br>5-[3-(3-Chlorobenzoylamino)1H-indazol-5-yl]-furan-2-carboxylic acid | 1.842 | A |
| "A18" | 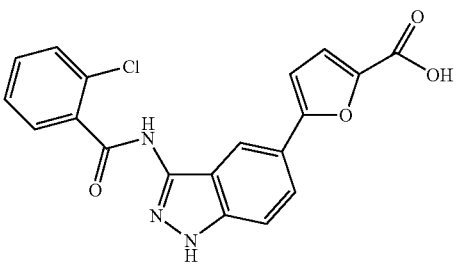<br>5-[3-(2-Chlorobenzoylamino)1H-indazol-5-yl]-furan-2-carboxylic acid | 1.703 | A |
| "A19" | 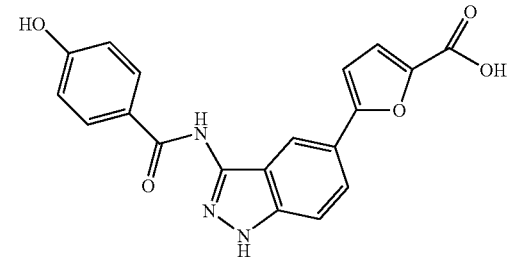<br>5-[3-(4-Hydroxybenzoylamino)1H-indazol-5-yl]furan-2-carboxylic acid | 1.534 | A |
| "A21" | 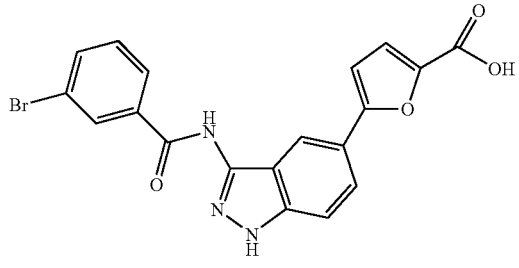<br>5-[3-(3-Bromobenzoylamino)1H-indazol-5-yl]-furan-2-carboxylic acid | 1.779 | A |

-continued

| No. | Chemical structure Name | Retention time Rf [min] | HPLC method |
|---|---|---|---|
| "A22" | 5-[3-(3-Fluorobenzoylamino)1H-indazol-5-yl]-furan-2-carboxylic acid | 1.655 | A |
| "A23" | 5-[3-(3-Ethylbenzoylamino)1H-indazol-5-yl]-furan-2-carboxylic acid | 1.806 | A |
| "A24" | 5-[3-(3-Trifluoromethylbenzoylamino)1H-indazol-5-yl]furan-2-carboxylic acid | 1.834 | A |
| "A25" | 5-[3-(3-Methylbenzoylamino)1H-indazol-5-yl]-furan-2-carboxylic acid | 1.702 | A |

| No. | Chemical structure Name | Retention time Rf [min] | HPLC method |
|---|---|---|---|
| "A26" | 5-[3-(3-Methoxybenzoylamino)1H-indazol-5-yl]furan-2-carboxylic acid | 1.636 | A |
| "A27" | 5-[3-(3-Hydroxybenzoylamino)1H-indazol-5-yl]furan-2-carboxylic acid | 1.455 | A |
| "A28" | 5-{3-[3-(2-Dimethylaminoethoxy)benzoylamino]1H-indazol-5-yl}furan-2-carboxylic acid | 1.482 | A |

The following examples relate to medicaments:

EXAMPLE A

Injection Vials

A solution of 100 g of an active ingredient according to the invention and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient according to the invention with 100 g of soya lecithin and 1400 g of cocoa butter is melted, poured into moulds and allowed to cool. Each suppository contains 20 mg of active ingredient.

EXAMPLE C

Solution

A solution is prepared from 1 g of an active ingredient according to the invention, 9.38 g of $NaH_2PO_4.2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient according to the invention are mixed with 99.5 g of Vaseline under aseptic conditions.

EXAMPLE E

Tablets

A mixture of 1 kg of active ingredient according to the invention, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

EXAMPLE F

Dragees

Tablets are pressed analogously to Example E and subsequently coated in a conventional manner with a coating of sucrose, potato starch, talc, tragacanth and dye.

EXAMPLE G

Capsules 2 kg of active ingredient according to the invention are introduced into hard gelatine capsules in a conventional manner in such a way that each capsule contains 20 mg of the active ingredient.

EXAMPLE H

Ampoules

A solution of 1 kg of active ingredient according to the invention in 60 l of bidistilled water is sterile filtered, transferred into ampoules, lyophilised under sterile conditions and sealed under sterile conditions. Each ampoule contains 10 mg of active ingredient.

The invention claimed is:
1. A compound of the formula

| No. | Chemical structure Name |
|---|---|
| "A5" | 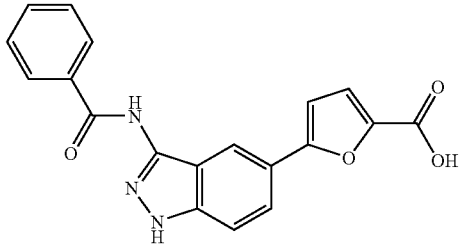<br>5-(3-Benzoylamino-1H-indazol-5-yl)furan-2-carboxylic acid |
| "A12" | 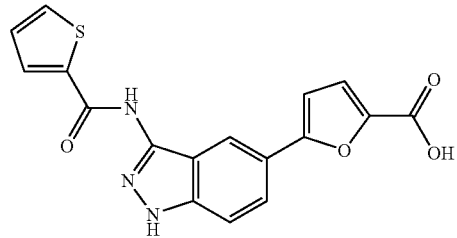<br>5-{3-[(Thiophene-2-carbonyl)amino]-1H-indazol-5-yl}-furan-2-carboxylic acid |
| "A17" | 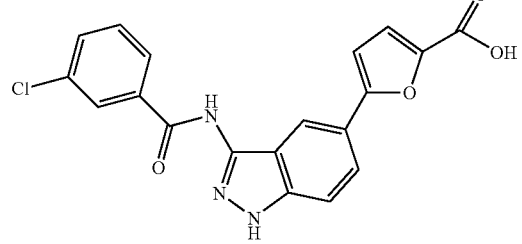<br>5-[3-(3-Chlorobenzoylamino)-1H-indazol-5-yl]furan-2-carboxylic acid |

| No. | Chemical structure Name |
|---|---|
| "A21" | 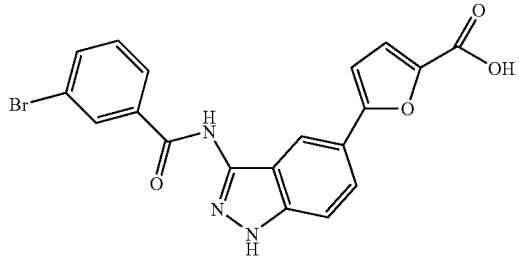<br>5-[3-(3-Bromobenzoylamino)-1H-indazol-5-yl]furan-2-carboxylic acid |
| "A22" | 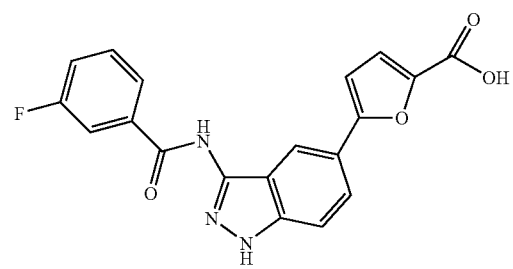<br>5-[3-(3-Fluorobenzoylamino)-1H-indazol-5-yl]furan-2-carboxylic acid |
| "A25" | 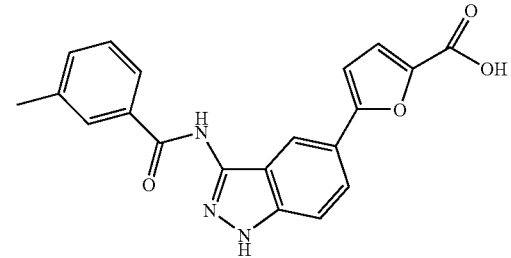<br>5-[3-(3-Methylbenzoylamino)-1H-indazol-5-yl]furan-2-carboxylic acid |
| "A27" | 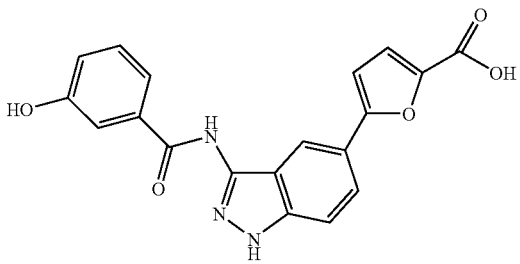<br>5-[3-(3-Hydroxybenzoylamino)-1H-indazol-5-yl]furan-2-carboxylic acid | or a pharmaceutically acceptable salt, tautomer or stereoisomer thereof, including mixtures thereof in all ratios.

2. A pharmaceutical composition comprising at least one compound according to claim 1 or a pharmaceutically acceptable salt, tautomer or stereoisomer thereof, including mixtures thereof in all ratios, and a pharmaceutically acceptable carrier.

3. A kit consisting of separate packs of
(a) an effective amount of a compound according to claim 1 or a stereoisomer thereof, including mixtures thereof in all ratios, and
(b) an effective amount of a further pharmaceutically active ingredient.

* * * * *